US009119391B1

(12) United States Patent
Perez et al.

(10) Patent No.: US 9,119,391 B1
(45) Date of Patent: *Sep. 1, 2015

(54) POLYMER COATED CERIA NANOPARTICLES FOR SELECTIVE CYTOPROTECTION

(75) Inventors: Jesus Manuel Perez, Orlando, FL (US); Atul Asati, Orlando, FL (US); Sudip Nath, Orlando, FL (US); Charalambos Kaittanis, Oviedo, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 1241 days.

This patent is subject to a terminal disclaimer.

(21) Appl. No.: 12/169,179

(22) Filed: Jul. 8, 2008

Related U.S. Application Data

(63) Continuation-in-part of application No. 11/965,343, filed on Dec. 27, 2007.

(60) Provisional application No. 60/949,953, filed on Jul. 16, 2007.

(51) Int. Cl.
  *A01N 59/16* (2006.01)
  *A61K 9/14* (2006.01)
  *A01N 1/02* (2006.01)

(52) U.S. Cl.
  CPC ........................................ *A01N 1/02* (2013.01)

(58) Field of Classification Search
  IPC .......... A01N 1/02,1/0226; A61K 33/00, 9/5161
  See application file for complete search history.

(56) References Cited

U.S. PATENT DOCUMENTS

| | | | |
|---|---|---|---|
| 5,089,860 A | 2/1992 | Deppe et al. | |
| 5,411,647 A | 5/1995 | Johnson et al. | |
| 5,486,359 A | 1/1996 | Caplan et al. | |
| 5,910,311 A | 6/1999 | Boussouira | |
| 5,961,993 A | 10/1999 | Boussouira | |
| 6,042,714 A | 3/2000 | Lin et al. | |
| 6,103,247 A | 8/2000 | Boussouira | |
| 6,139,985 A | 10/2000 | Borglum et al. | |
| 6,316,012 B1 | 11/2001 | N'Guyen | |
| 6,327,074 B1 | 12/2001 | Bass et al. | |
| 6,368,577 B1 | 4/2002 | Kropf et al. | |
| 6,406,685 B1 | 6/2002 | Philippe | |
| 6,468,551 B1 | 10/2002 | Diec | |
| 6,497,863 B1 | 12/2002 | Wachter | |
| 6,497,865 B1 | 12/2002 | Griesbach | |
| 6,501,590 B2 | 12/2002 | Bass et al. | |
| 6,592,746 B1 | 7/2003 | Schmid-Schoenbein et al. | |
| 6,654,161 B2 | 11/2003 | Bass et al. | |
| 6,844,387 B2 | 1/2005 | Bass et al. | |
| 6,890,896 B1 | 5/2005 | Shashoua | |
| 6,953,532 B2 * | 10/2005 | Lee et al. ........................ 216/89 |
| 7,005,504 B2 | 2/2006 | Hsei et al. | |
| 7,075,707 B1 | 7/2006 | Rapaport et al. | |
| 7,141,227 B2 | 11/2006 | Chan | |
| 7,270,813 B2 | 9/2007 | Shimp et al. | |
| 7,347,987 B2 | 3/2008 | McGinnis et al. | |
| 7,431,758 B2 | 10/2008 | Ota et al. | |
| 7,442,686 B2 | 10/2008 | Lasko et al. | |
| 7,471,706 B2 | 12/2008 | Bass et al. | |
| 7,504,356 B1 | 3/2009 | Self et al. | |
| 7,507,480 B2 | 3/2009 | Sugama | |
| 7,534,453 B1 * | 5/2009 | Rzigalinski et al. .......... 424/617 |
| 7,563,459 B2 | 7/2009 | Phillips et al. | |
| 7,642,250 B2 | 1/2010 | Williams | |
| 7,687,505 B2 | 3/2010 | Sugaya | |
| 7,725,802 B2 | 5/2010 | Eroz et al. | |
| 7,772,375 B2 | 8/2010 | Greferath et al. | |
| 7,888,119 B2 | 2/2011 | Sugaya et al. | |
| 7,899,093 B1 | 3/2011 | Bass et al. | |
| 7,906,147 B2 | 3/2011 | Hainfeld et al. | |
| 7,914,617 B2 | 3/2011 | Yadav | |

(Continued)

FOREIGN PATENT DOCUMENTS

WO  WO 99/15891  6/1995
WO  WO 03/059263 A2  7/2003

(Continued)

OTHER PUBLICATIONS

Robert T. Magari. 2003. Assessing shelf life using real-time and accelerated stability tests. Biopharm International, vol. 16, Issue 11, pp. 36-43.*

Srivaisan Sathyamurthy, et al., "Reverse Micellar Synthesis of Cerium Oxide Nanoparticles" Nanotechnology, 16, (2005) pp. 1960-1964.

S. Patil, et al., "Synthesis of Nanocrystalline Ceria Particles for High Temperature Oxidation Resistant Coating" Journal of Nanoparticle Research, 4, (2002) pp. 433-438.

(Continued)

*Primary Examiner* — Debbie K Ware
*Assistant Examiner* — Kailash C Srivastava
(74) *Attorney, Agent, or Firm* — Timothy H. Van Dyke; Beusse, Wolter, Sanks & Maire, PLLC

(57) ABSTRACT

Methods, systems and compositions are disclosed wherein normal, non-transformed, healthy biological cells are protected from oxidative stress, radiation therapy and chemotherapy while diseased, transformed cells, such as, cancer cells, are provided no protection by the biocompatible, polymer coated nanoceria composition of the present invention. The polymer-coated nanoceria preparation herein exhibits no toxicity to normal cells and exhibits pH-dependent antioxidant properties at neutral or physiological pH values, between approximately 6.5 to approximately 11.0 and is inactive as an antioxidant at acidic pH values between approximately 2.0 to approximately 6.4. Improved therapeutic agents and cytoprotecting devices are based on the newly discovered, pH dependent properties of polymer-coated nanoceria that provide selective cytoprotection.

12 Claims, 21 Drawing Sheets

(56) References Cited

U.S. PATENT DOCUMENTS

| | | | |
|---|---|---|---|
| 7,959,949 | B2* | 6/2011 | Seal et al. ............... 424/489 |
| 8,080,420 | B2 | 12/2011 | Sugaya |
| 8,097,270 | B2 | 1/2012 | Ketelson et al. |
| 8,172,901 | B2 | 5/2012 | Altman et al. |
| 8,333,993 | B1* | 12/2012 | Perez et al. ............... 424/489 |
| 2003/0050709 | A1 | 3/2003 | Noth et al. |
| 2003/0124194 | A1 | 7/2003 | Gaw et al. |
| 2003/0187077 | A1 | 10/2003 | Chane-Ching |
| 2004/0062753 | A1 | 4/2004 | Rezania et al. |
| 2005/0130167 | A1 | 6/2005 | Bao et al. |
| 2005/0159820 | A1 | 7/2005 | Yoshikawa et al. |
| 2005/0164377 | A1 | 7/2005 | Miyabayashi et al. |
| 2005/0171192 | A1 | 8/2005 | Gehlsen |
| 2006/0014938 | A1 | 1/2006 | Groman et al. |
| 2006/0110440 | A1 | 5/2006 | Sugaya et al. |
| 2006/0142749 | A1 | 6/2006 | Ivkov |
| 2006/0280729 | A1 | 12/2006 | Mistry |
| 2007/0003621 | A1 | 1/2007 | Nangia et al. |
| 2009/0087493 | A1 | 4/2009 | Dai et al. |
| 2009/0098574 | A1 | 4/2009 | Brisson et al. |
| 2010/0151000 | A1 | 6/2010 | Thomas et al. |
| 2010/0166821 | A1* | 7/2010 | Rzigalinski et al. .......... 424/423 |

FOREIGN PATENT DOCUMENTS

| | | |
|---|---|---|
| WO | WO 2006/118954 | 11/2006 |
| WO | WO 2006/118954 A2 | 11/2006 |
| WO | WO 2007/002662 | 1/2007 |
| WO | WO 2007/002662 A2 | 1/2007 |
| WO | WO 2008/064357 A2 | 5/2008 |
| WO | PCT/US2009/041675 | 6/2009 |
| WO | WO 2009/132277 A1 | 10/2009 |

OTHER PUBLICATIONS

H.S. Potdar, et al. "Preparation of ceria-ziconia (Ce0.75Zr0.25O2) powders by microwave-hydrothermal (MH) route" Materials Chemistry and Physics, 74, (2002) pp. 306-312.

David Schubert, et al., "Cerium and yttrium oxide nanoparticles are neuroprotective" Biochemical and Biophysical Research Communications, 342, (2006) pp. 86-91.

Mukesh G. Harisinghani, et al., "Noninvasive Detection of Clinically Occult Lymph-Node Metastases in Prostate Cancer" New England Journal of Medicine, vol. 348, No. 25, (Jun. 19, 2003) pp. 2491-2500.

Rzigalinski, et al. Cerium oxide nanoparticies increase the lifespan of cultured brain cells and protect against free radical and mechanical trauma, FASEB Journal, 2003, pp. A606, vol, 17, No. 4-5, Abstract No. 3377.24.

Niu, et al., Cardioprotective effects of cerium oxide nanoparticles in a transgenic murine model of cardiomyopathy, Cardiovas. Res., 2006, pp. 549-559, vol. 73, No. 3.

Qureshi, et al. Increased exhaled nitric oxide following autologous peripheral hemotopietic stem-cell transplantation: a potential marker of idopathic pneumonia syndrome, Chest, 2004, pp. 281-287, vol. 125, No. 1.

Ohgushi, et al., Stem cell technology and bioceramics: from cell to gene engineering, J. Biomed. Mat. Res., 1999, pp. 913-927, vol. 48, abstract.

Dal Maschio, et al., Influence of Ce3+/Ce4+ ratio on phase stability and residual stress held in ceria-yttria stabilized zirconia plasma-sprayed coatings, J. Mat. Sci., 1992, pp. 5591-5596, vol. 27, abstract.

Ramsfjell, et al., Distinct requirements for optimal growth and in vitro expansion of human CD34+ CD38- bone marrow long-term culture-initiating cells (LTC-IC), extended LTC-IC, and murine in vivo long-term reconstituting stem cells, Blood, 1999, pp. 4093-4102, vol. 99, No. 12, abstract.

Devasenpathi, et al., Forming near net shape free-standing components by plasma spraying, Mat. Let., 2002, pp. 882-886, vol. 57.

Imamura, et al., Drusen, choroidal neovascularization, and retinal pigment epithelium dysfunction in SOD1-deficient mice: a model of age-related macular degeneration, PNAS, 2006, pp. 11282-11287, vol. 103, No. 30.

Hollyfield, et al., Oxidative damage-induced inflammation initiates age-related macular degeneration, Nature Medicine, 2008. pp. 194-198, vol. 14.

Birch, et al., Age-related macular degeneration: a target for nanotechnology derived medicines, International Journal of Nanomedicine. 2007, pp. 65-77, vol. 2, No. 1.

Maulik, N., Reactive oxygen species drives myocardial angiogenesis?, Antioxidants & Redox Signaling, 2006, pp. 2161-2168, vol. 8, Nos. 11-12.

McGinnis, et al. U.S. Appl. No. 12/772,523 Office Action mailed Sep. 15, 2011.

Ohia, et al., Pharmacological consequences of oxidative stress in ocular tissues, Mutation Research. 2005, pp. 22-36, vol. 579.

Liu, et al. Subtype lesions of neovascuiar age-related macular degeneration in Chinese patients, Braefe's Arch Clin Exp Opthalmol, 2007, pp. 1441-1445, vol. 245.

Silva, Seeing the benefits ceria, Nature Nanotechnology, 2006 pp. 92-94, vol. 1.

Hahn, et al., Maculas affected by age-related macular degeneration contain increased chelatable iron in the retinal pigment epithelium and Bruch's membrane, Arch. Opthalmol., 2003, pp. 1099-1105, vol. 121.

Haywood, et al., Inflammatlon and angiogenesis in osteoarthritis, Arthritis & Rheumatism, 2003, pp. 2173-2177, vol. 48, No. 8.

Chen, et al., Rare earth nanoparticles prevent retinal degeneration induced by intracellular peroxides, Nature Nano Technology, 2006, pp. 142-148, vol. 1, No. 2, abstract.

Moongkarndi, et al., Antiproliferation, antioxidation and induction of apoptosis by *Carcina mangostana* (mangosteen) on SKBR3 human breast cancer cell line, J. of Ethno-Pharmacology, 2004, pp. 161-166, vol. 90, abstract.

Margrain, et al., Do blue light filters confer protection against age-related macular degeneration?, Progress in Retinal and Eye Research, 2004, pp. 523-531, vol. 23, abstract.

Bailey, et al., Cerium oxide nanoparticles extend cell longevity and act as free radical scavengers, online, retrieved on Apr. 24, 2006, retrieved from http://www.med.miami.edu/mnbws/Rzigalinski11.html, abstract.

Tsai, The study of the synthesis of nano-grade cerium oxide powder, Materials Letters, 2004, pp. 2270-2274, vol. 58, abstract.

Rzigalinski, et al., Ceriurn oxide nanopartides increase the lifespan of cultured brain cells and protect against free radical mechanical trauma, FASEB Journal, 2003, vol. 17, No. 4-5, p. abstract No. 377.24, abstract.

Cook, et al., Neuronal damage induced by polychlorinated biphenyls is partially reversed by cerium oxide nanoparticles, online, 2003, retrieved from http://sfn.schoiarone.com/itin2003/main.html?new_page_id=126&abstract_id=14513&p_num=669.13&is_tech=0>, retrieved on Aug. 5, 2008, abstract.

Tusnekawa, S., et al., Lattice relaxation of monosize CeO2-x nanocrystalline particles, Applied Surface Science Elsevier Netherlands, 1999, pp. 53-56, vol. 152, No. 1-2, abstract.

Hooper, et al., New treatment in age-related macular degeneration, Clinical Experimental Opthalmology, 2003, pp. 376-391, vol. 31, abstract.

Suzuki, et al., Preparation and characteristics of magnetite-labelled antibody with the use of poly(ethylene glycol) derivatives Biotech. and Applied Biochem., 1995, pp. 335-345, vol. 21.

Dung, et al., Activation of glassy carbon electrodes by dispersed metal oxide particles, Dept. of Chemistry, OSU, downloaded 2011, pp. 813, abstract.

Shui, et al., Morphological observation on cell death and phagocytosis induced by ultraviolet irradiation in a cultured human lens epithelial cell line, Exp. Eye Res., 2000, pp. 608-619, vol. 71, No. 6, abstract.

Xijuan, et al., Size-dependent optical properties of nanocrystalline CeO2:Er obtained by combustion synthesis, Phys. Chem., 2001, pp. 5266-5269, vol. 3, abstract.

Guo, Green and red upconversion luminescence in CeO2:Er3+ powders produced by 785 nm laser, Journal of Solid State Chemistry, 2007, pp. 127-131, vol. 180, 1, abstract.

(56) References Cited

OTHER PUBLICATIONS

Perez, et al., Synthesis of biocompatible dextran-coated nanoceria with pH-Dependent antioxidant properties, Small, 2008, pp. 552-556, vol. 4, No. 5, abstract.

Pirmohamed, et al., Nanoceria exhibit redox state-dependent catalase mimetic activity, Chem. Comm, 2010, pp. 2736-2738, vol. 46, abstract.

Chen, et al., Rare earth nanoparticles prevent retinal degeneration induced by intracellular peroxides, Nature Publishing Group, 2006, pp. 1-9, abstract.

Karakoti, et al., Direct synthesis of nanoceria in aqueous polyhydroxyl solutions, J. Phys. Chem. C, 2007, pp. 17232-17240, vol. 111, No. 46, abstract.

Tarnuzzer, et al., Vacancy engineered ceria nanostructures for protection from radiation-induced cellular damage, Nano Lett, 2005, pp. 2573-2577, vol. 4, No. 12, abstract.

Heckert, et al., The role of cerium redox state in the SOD mimetic activity of nanoceria, Biomaterials, 2008, pp. 2705-2709, vol. 29, abstract.

Schubert, et al., Cerium and yttrium oxide nanoparticles are neuroprotective, Biochemical and Biophysical Research Communications, 2006, pp. 86-91, vol. 342.

Zhang, et al., Cerium oxide nanoparticles: size selective formation and structure analysis, Applied Physics Letters, 2002, pp. 127-129, vol. 81, No. 1.

Patil, et al., Surface-derived nanoceria with human carbonic anhydrase II inhibitors and flourphores: a potential drug delivery device, J. Phys. Chem. C., 2007, pp. 8437-8442, vol. 111, No. 24, abstract.

Patil, et al., Synthesis of nanocrystalline ceria particles for high temperature oxidation resistant coating, Journal of Nanoparticle Research, 2002, pp. 433-438, vol. 4, abstract.

Jin, et al., Nanopartical-mediated drug delivery and gene therapy, Biotechnol. Prog, 2007, pp. 32-41, vol. 23, abstract.

Eck, et al., PEGylated gold nanoparticles conjugated to monoclonal F19 antibodies as targeted labeling agents for human pancreatic carcinoma tissue, ACS Nano, 2008, pp. 2263-2272, vol. 2, No. 11, abstract.

Nafee, Dissertation entitled "Cationically-modified nanoparticles for the polmonary delivery of the telomerase inhibitor 2'-O-Methyl RNA for the treatment of lung cancer," Dissertation zur Erlangung des Grades des Doktors der, Naturwissenschaftem der Naturwissenschaftilch-Technischen Fakul't III Chemie, Pharmazie, Bio-und Werstoffwisserischaften der Universit des Saarlandes, 2008, abstract.

Nazem, et al,, Nanotechnology for Alzheimer's disease detection and treatment, Insciences J., 2011, pp. 169-193, vol. 1, No. 4, abstract.

Oliver, et al., Synthesis of pegylated immunonanoparticles, Pharmaceutical Research, 2002, pp. 1137-1143, vol. 19, No. 8, abstract.

Otsuka, et al., PEGylated nanoparticles for biological and pharmaceutical applications, Advanced Drug Delivery Reviews, 2003, pp. 403-419, vol. 55, abstract.

Qi, et al., Redispersible hybrid nanopowders; cerium oxide nanoparticle complexes with Phosphonated-PEG pligomers, ACS Nano, 2008, pp. 879-888, vol. 2, No. 5, abstract.

Sokolov, et al., Real-time vita optical imaging of precancer using anti-epidermal growth factor receptor antibodies conjugated to gold nanoparticles, Cancer Res. 2003. vol. 63, abstract.

Suh, et al., Multifunctional nanosystems at the interface of physical and life sciences, Physicaplus, 2010, issue 13, abstract.

\* cited by examiner

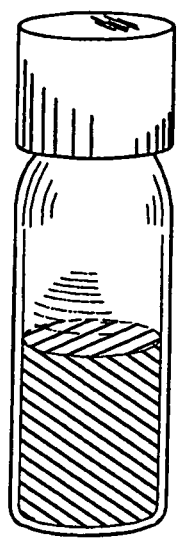 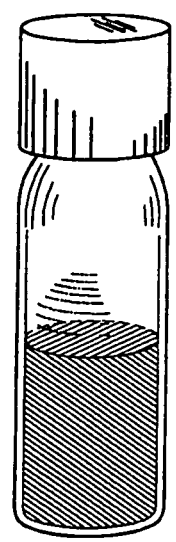
Fig. 6A
Fig. 6B
Photographic image of a first solution of dextran coated nanoceria.
Photographic image of a second solution of dextran coated nanoceria.

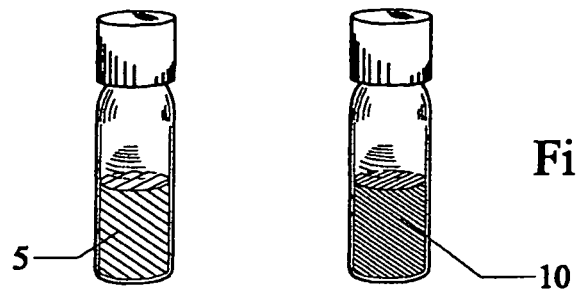
Fig. 10A (Day 1)
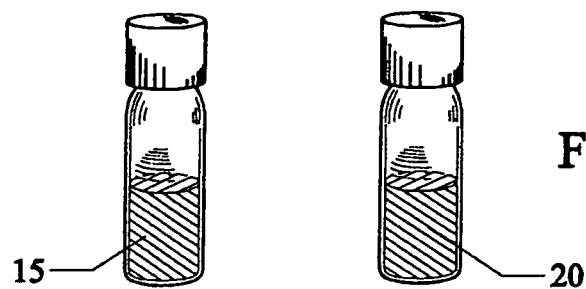
Fig. 10B (Day 3)
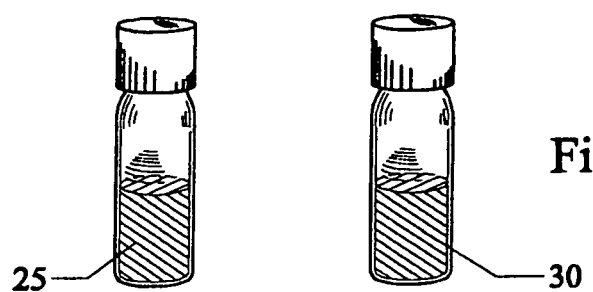
Fig. 10C (Day 7)
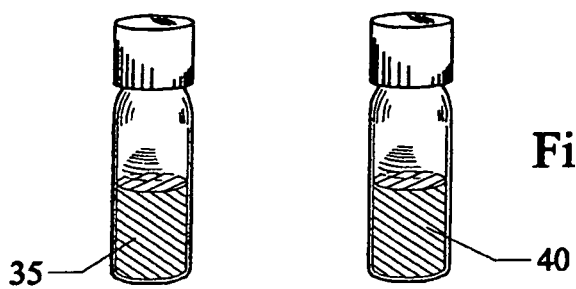
Fig. 10D (Day 10)

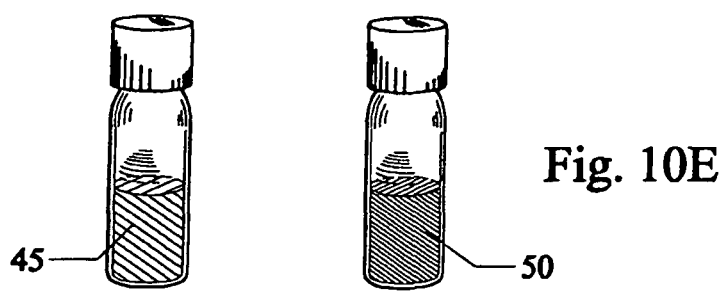
After adding fresh hydrogen peroxide on 10th day
Fig. 10E
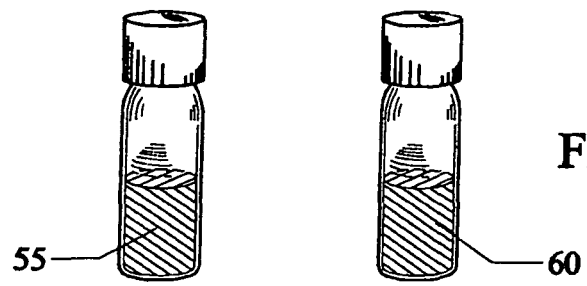
Fig. 10F (Day 20)

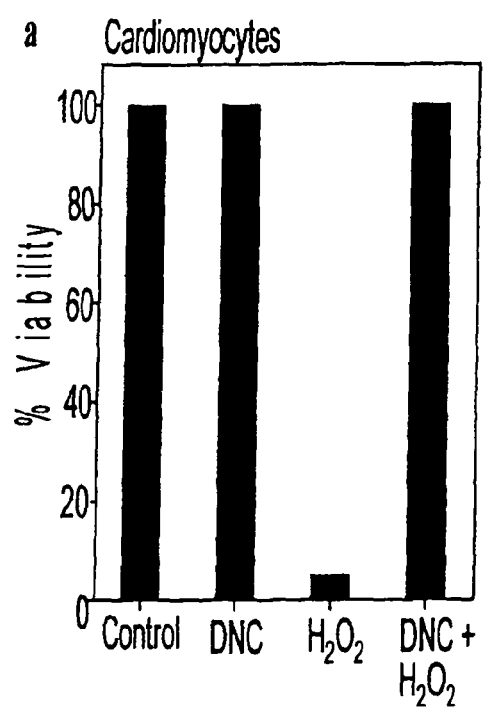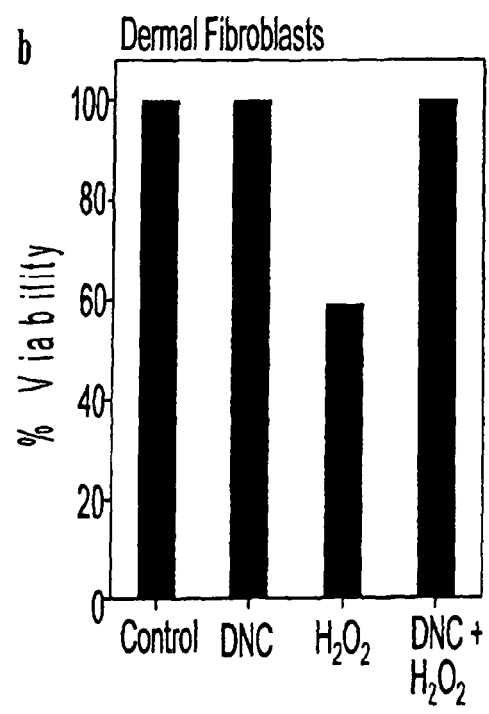
Figure 11A                                   Figure 11B

Figure 17A                    Figure 17B
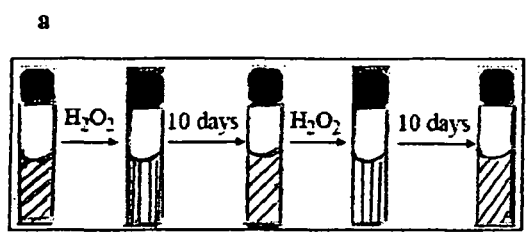
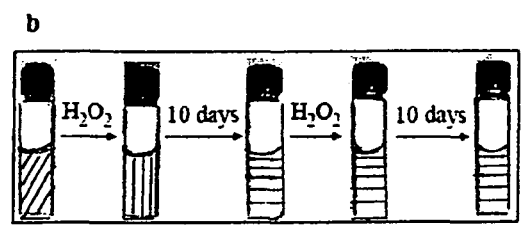
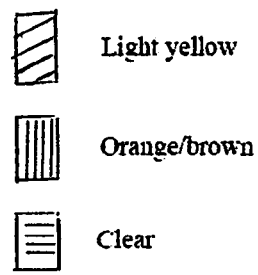
Light yellow
Orange/brown
Clear

US 9,119,391 B1

POLYMER COATED CERIA NANOPARTICLES FOR SELECTIVE CYTOPROTECTION

RELATED APPLICATIONS

The present application claims the benefit of priority from U.S. Provisional Patent Application Ser. No. 60/949,953 filed on Jul. 26, 2007 and is a continuation-in-part of U.S. patent application Ser. No. 11/965,343 filed on Dec. 27, 2007, both applications are incorporated herein by reference.

This invention was made with Government support under Agency contract number K01 CA101781 awarded by the National Institutes of Health. The government has certain rights in this invention.

FIELD OF THE INVENTION

This invention relates to biological uses of nanoceria particles, and in particular to methods, systems and compositions useful in the synthesis of polymer coated ceria oxide nanoparticles for biomedical applications.

BACKGROUND AND PRIOR ART

Cerium is a silvery metallic element, belonging to the lanthanide group. Cerium oxide ($Ce_2O_3$/$CeO_2$) is used in precision polishing and lapping applications. Ultra fine nanosize cerium oxide, less than 10 nanometers, is more efficient for coating purposes. Recently, it was reported by B. Rzigalinski et al. that nanoparticles prolong the life of cortical neurons in culture 4 fold over the cells without treatment, decrease the intracellular Ca2+ concentration and prevent UV damage of cortical neurons. See B. Rzigalinski et al., "Cerium Oxide Nanoparticles Extend Cell Longevity and Act as Free Radical Scavengers" at website http://www.med.miami.edu/mnbws/Rzigalinski112.html. Based on its chemical characteristics, this effect is partially due to a decrease of reactive oxygen species (ROS).

Various investigators have shown that nanoceria particles possess antioxidant properties and have demonstrated the survival of neuron cells in cultures against oxidative stress and radiation.

However, the synthetic procedures for nanoceria reported so far are not likely to be approved by the U.S. Food and Drug Administration (FDA) because the synthesis procedures involve the use of surfactants and other toxic materials.

In addition, the published synthetic methods result in uncoated nanoparticles that are not stable and tend agglomerate in aqueous solutions.

Further developments in biomedical research reveal the efficacy of coated magnetic nanoscale particle compositions for therapeutic uses. In Patent Publication WO/2003/005029 to Zhenghe Xu et al. iron and iron oxide particles are coated with dextran for biological cell separation using magnetic carrier technology. The dextran coating is used to prevent mechanical instability of the particle in suspension.

U.S. Patent Publication 2003/0124,194 to Gaw et al. discloses amine functionalized superparamagnetic nanoparticles using a process that consists of coating the magnetic nanoparticles with a carboxylated polymer then subsequently reacting the carboxylated functionalized magnetic nanoparticles with carbodiimide and a large excess of diamine, after which the amine-terminated nanopartices are reacted with bifunctional crosslinking agents and various biomolecules.

U.S. Patent Publication 2005/0130167 to Gang Boa, et al. provides multifunctional magnetic nanoparticle probe compositions for molecular imaging and monitoring wherein the magnetic nanoparticle has a biocompatible coating, such as, dextran, thereon.

U.S. Patent Publication 2006/0014938 to Groman et al. describes stable aqueous colloidal lanthanide oxides, including cerium oxide, some of which are associated with a polymer, including dextran. The colloidal compositions are useful as imaging agents in technology requiring injectable chemicals for contrast agents. There is no mention of cerium oxide coated with polymers having autocatalytic and antioxidant properties.

U.S. Patent Publication 2006/0142749 to Robert Ivkov discloses thermotherapeutic compositons for treating disease. The thermotherapeutic compositions include magnetic nanoparticles that may be coated to enhance the heating properties of a bioprobe, particularly if the coating is a polymeric material that can include dextran.

Thus, polymeric coatings including dextran have been reported for use on magnetic nanoparticles and the results seem promising in molecular imaging, monitoring and therapeutic treatment of disease.

In addition, prior to the present invention, most synthetic procedures for nanoceria resulted in nanoparticles with poor water solubility and provided ceria particles that precipitate from aqueous solutions. Also, prior art synthetic procedures involve the use of toxic solvents, therefore hindering their potential clinical use.

It is desirable to find reliable solutions to use of nanoceria particles with antioxidant properties in the treatment of many human diseases that are due to the death of cells in specific tissues or organs. The majority of those diseases are due to accumulation of metabolic insults from reactive oxygen species originating within or outside of the cells. These diseases include all forms of blindness whether hereditary, light-induced, or physical damage such as occurs in retinal detachment. In addition, damage due to ageing, stroke, cardiac infarction, burns, etc, which proceed through reactive oxygen species, can be addressed with the nanoceria particles synthesized according the present invention.

The ability of nanoceria particles to reversibly switch from $Ce^{+3}$ to $Ce^{+4}$ is a key factor in their use in catalytic and biological applications as antioxidants. In co-pending U.S. application Ser. No. 11/965,343 filed on Dec. 27, 2007, it was reported that the polymeric coating does not affect the autocatalytic properties of nanoceria, as hydrogen peroxide and peroxyl radicals can diffuse through the hydrophilic polymer coating and oxidize $Ce^{+3}$ to $Ce^{+4}$. Thus, polymer-coated nanoceria particles are used as antioxidants in biomedical applications, such as, protection against radiation damage, oxidative stress and inflammation.

The present application shows that polymer-coated nanoceria particles with enhanced biocompatibility and stability in aqueous solution exhibit a pH-dependent antioxidant activity and provide a means for tailoring reversible and non-reversible antioxidant properties of polymer-coated nanoceria particles.

SUMMARY OF THE INVENTION

The objectives of U.S. application Ser. No. 11/965,343 filed on Dec. 27, 2007, are also objectives of the present invention and are listed below.

A primary objective of the present invention is to provide a facile, synthetic method for the formation of cerium oxide (ceria) nanoparticles coated with a biodegradable polymer.

A secondary objective of the present invention is to provide a synthetic method for the formation of cerium oxide (ceria)

nanoparticles coated with dextran, a biodegradable polymer that can be scaled up for commercial production.

A third objective of the present invention is to provide cerium oxide (ceria) nanoparticles coated with a biodegradable polymer that has physical properties that are substantially identical of the properties of uncoated nanoceria particles for therapeutic applications.

A fourth objective of the present invention is to provide cerium oxide (ceria) nanoparticles coated with a biodegradable polymer with good solubility and stability in water and phosphate buffered saline, with no precipitation for approximately 12 months.

A fifth objective of the present invention is to provide a facile, synthetic method for the formation of cerium oxide (ceria) nanoparticles coated with dextran that is further crosslinked with epichlorohydrin and treated with ammonia, resulting in an aminated dextran coated ceria nanoparticles to create a targetable ceria nanoparticle.

A sixth objective of the present invention is to provide a water stable, biodegradable polymer coated nanoceria preparation that is biologically active for administration to human and other mammals.

A seventh objective of the present invention is to provide a water stable, biodegradable polymer coated nanoceria preparation that has a long circulation time, such as, a plasma half-life longer than one minute.

An eighth objective of the present invention is to provide a facile, synthetic method for the formation of cerium oxide (ceria) nanoparticles coated with polyacrylic or any other polycarboxylic acid polymer that will result in a carboxyl group functionalized nanoparticle. The ceria nanoparticles coated with functionalized carboxyl groups are reacted with a diamine, such as ethylenediamine, to create an amine functionalized cerium oxide nanoparticle without the need for polymeric crosslinking.

Additional objectives of the continuation-in-part application are as follows:

A ninth objective of the present invention is to provide polymer-coated ceria nanoparticles formed in situ for use in improved therapeutic agents and cytoprotecting devices.

A tenth objective of the present invention is to provide a biocompatible nanoceria preparation that protects normal cells against oxidative stress, while providing no cytoprotection to cancer or malignant cells.

A eleventh objective of the present invention is to provide smart, pH-dependent therapeutic agents and devices using polymer-coated ceria nanoparticles that selectively protect healthy tissue and cells from free radicals, but do not protect transformed cell lines due to the acidic microenvironment of the transformed cells.

A twelfth objective of the present invention is to provide pH-dependent therapeutic agents and devices using polymer-coated ceria nanoparticles that exhibit reversible and non-reversible antioxidant behavior.

A preferred in situ method for the synthesis of a plurality of cerium oxide nanoparticles coated with a biodegradable polymer for antioxidant, free-radical scavenging and autocatalytic biomedical applications, includes preparing an aqueous cerium nitrate solution, mixing the aqueous cerium nitrate solution with a biodegradable polymer to form a first mixture, adding the first mixture dropwise to an ammonium hydroxide solution while continuously stirring to form a second mixture, centrifuging the second mixture containing ammonium hydroxide to settle any debris or large particles, purifying the centrifuged mixture by ultrafiltration, and recovering a plurality of non-agglomerated cerium oxide nanoparticles coated with the biodegradable polymer wherein the antioxidant, free-radical scavenging and autocatalytic properties of the cerium oxide nanoparticles are unchanged from uncoated cerium oxide nanoparticles.

The preferred in situ synthesis method has a biodegradable polymer that is at least one of a carbohydrate polymer, a synthetic polyol, a carboxylated polymer, and derivatives thereof, more preferably, the carboxylated polymer is polyacrylic acid.

It is also preferred that the carboxylated polymer is reacted with a diamine selected from at least one of ethylene diamine, propylene diamine and hexane diamine, to provide an aminated cerium oxide nanoparticle in a reaction that eliminates the need for polymer crosslinking.

The preferred carbohydrate polymer for the in situ synthesis method of the present invention is a polysaccharide, such as dextran, arabinogalactan, chitosan and the like; most preferably the polysaccharide is dextran.

In the preferred in situ synthesis method the cerium nitrate solution contains approximately 2.0 to approximately 3.0 grams of cerium nitrate to approximately 5 ml of water and the plurality of dextran-coated cerium oxide nanoparticles has a UV profile exhibiting strong absorption below approximately 400 nm with peak absorption at approximately 300 nm.

A preferred composition that is useful as a potent antioxidant in biomedical applications includes a plurality of nanoceria particles coated with a biodegradable polymer selected from at least one of a carbohydrate polymer, a synthetic polyol, a carboxylated polymer, and derivatives thereof. The more preferred carboxylated polymer is polyacrylic acid. The preferred carbohydrate polymer is a polysaccharide, such as, dextran, arabinogalactan and chitosan; most preferably, the polysaccharide is dextran.

In the preferred composition, the plurality of dextran-coated cerium oxide nanoparticles has a UV profile exhibiting strong absorption below approximately 400 nm with peak absorption at approximately 300 nm and the physical properties of the dextran-coated cerium nanoparticles replicate the physical properties of the uncoated nanoceria particles for therapeutic applications as antioxidants, free-radical scavengers and autocatalytic agents.

In the preferred composition, the plurality of dextran-coated cerium oxide nanoparticles form a colloidal suspension that is stable in water and form a colloidal suspension that is stable in a phosphate buffer saline solution.

A more preferred composition of matter that is useful as an antioxidant, free-radical scavenger and autocatalyst in biomedical applications includes a plurality of nanoceria particles coated with a crosslinked-aminated biodegradable polymer selected from at least one of a carbohydrate polymer, a synthetic polyol, a carboxylated polymer, and derivatives thereof. The preferred carbohydrate polymer is a polysaccharide such as, dextran, arabinogalactan and chitosan; the most preferred polysaccharide is dextran.

The preferred composition has a plurality of dextran-coated cerium oxide nanoparticles with a UV profile exhibiting strong absorption below approximately 400 nm with peak absorption at approximately 300 nm and the physical properties of the dextran-coated cerium nanoparticles replicate the physical properties of the uncoated nanoceria particles for therapeutic applications as antioxidants, free-radical scavengers and autocatalytic agents.

The more preferred composition has a plurality of dextran-coated cerium oxide nanoparticles that form a colloidal suspension that is stable in water and also form a colloidal suspension that is stable in a phosphate buffered saline solution.

Further objects and advantages of the present invention will be apparent from the following detailed description of a presently preferred embodiment which is illustrated schematically in the accompanying drawings.

BRIEF DESCRIPTION OF THE FIGURES

FIG. 6A is a photographic image of a first solution of dextran coated nanoceria after ultrafiltration with an Amicon 30 K filter.

FIG. 6B is a photographic image of a second solution of dextran coated nanoceria after the solution is concentrated using a 30K Centricon concentrator.

FIG. 10A is a real-time image of dextran nanoceria solutions without hydrogen peroxide on the left and with hydrogen peroxide on the right at day one.

FIG. 10B is a real-time image of dextran nanoceria solutions without hydrogen peroxide on the left and with hydrogen peroxide on the right at day three.

FIG. 10C is a real-time image of dextran nanoceria solutions without hydrogen peroxide on the left and with hydrogen peroxide on the right at day seven.

FIG. 10D is a real-time image of dextran nanoceria solutions without hydrogen peroxide on the left and with hydrogen peroxide on the right at day ten.

FIG. 10E is a real-time image of dextran nanoceria solutions without hydrogen peroxide on the left and with hydrogen peroxide on the right at day ten after adding fresh hydrogen peroxide.

FIG. 10F is a real-time image of dextran nanoceria solutions without hydrogen peroxide on the left and with hydrogen peroxide on the right at day twenty.

FIG. 11A is a graph showing the percent viability of normal cardiomyocyte cell cultures untreated and treated with dextran coated nanoparticles, hydrogen peroxide and a combination of dextran coated nanoparticles and hydrogen peroxide.

FIG. 11B is a graph showing the percent viability of normal dermal fibroblasts cell cultures untreated and treated with dextran coated nanoparticles, hydrogen peroxide and a combination of dextran coated nanoparticles and hydrogenperoxide.

FIG. 17A shows reversible color changes in a solution of dextran-coated nanoceria at pH 7.4, on addition of hydrogen peroxide.

FIG. 17B shows irreversible color changes in a solution of dextran-coated nanoceria at pH 4.0, on addition of hydrogen peroxide.

DESCRIPTION OF THE PREFERRED EMBODIMENTS

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

The term "nanoceria" is used interchangeably with "cerium oxide nanoparticles" and is used to refer to the cerium oxide particles of multiple valences.

The term "biodegradable polymer" is used herein to describe a class of polymers that are non-toxic to mammals and the environment and more specifically, include dextran, derivatives of dextran such as reduced dextran, carboxyl methyl reduced dextran, a polyol polymer or carbohydtrate polymer, synthetic polyols, carboxylated polymers, such as polyacrylic acid, and other polysaccharides, such as, but not limited to, arabinogalactan, and chitosan as disclosed in Groman et al. U.S. Patent Publication 2006/0014938 and Gaw et al. U.S. Patent Publication 2003/0124,194.

In the present invention, the cerium oxide nanoparticles or nanoceria are polymer associated, or, in other words, coated with a biodegradable polymer. The polymer confers stability in water and can be functionalized with carboxylic or amino groups for conjugation with proteins, peptides, oligonucleotides, small molecules, and the like.

Further, as will be explained in detail, the antioxidant activity of the polymer coated nanoceria particles is significantly reduced in a acidic pH, from approximately 2 to approximately 6; however, in the pH range from approximately 7 to approximately 11, the polymer-coated nanoceria particles are very active antioxidants, thus permitting the design of improved therapeutic devices, such as, in the radioprotection of healthy tissue during radiation therapy of acidic tumors.

Figure 14:
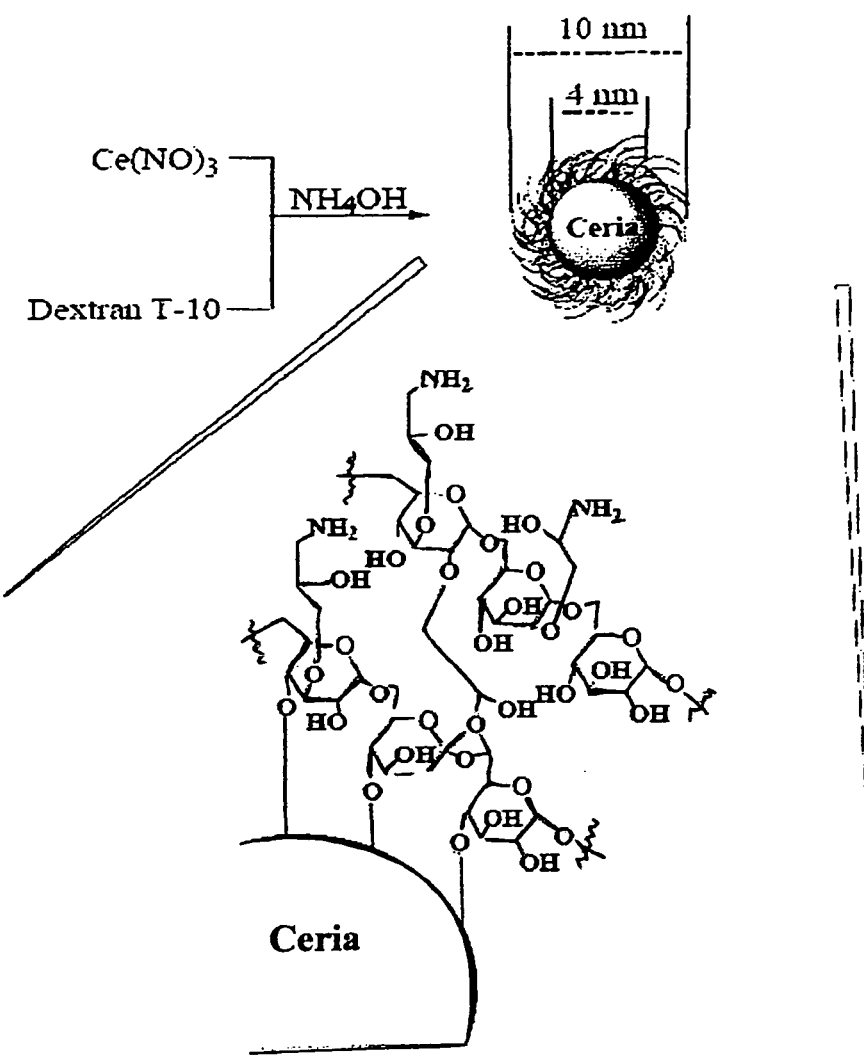
FIG. 14 is a diagram depicting the in-situ formation of stable cerium oxide nanoparticles coated with dextran polymer as stabilizer.

In general, the polymer coated nanoceria particles of the present invention each have a size between approximately 1 nanometer (nm) to approximately 500 nm in diameter, preferably between approximately 1 nm and approximately 10 nm. For example, the nanoceria particles used herein are composed of a cerium oxide core that is approximately 4 nanometers (nm) in diameter surrounded by a dextran coating for a total nanoparticle size of approximately 10 nm in diameter, as illustrated in FIG. 14.

Figure 8:
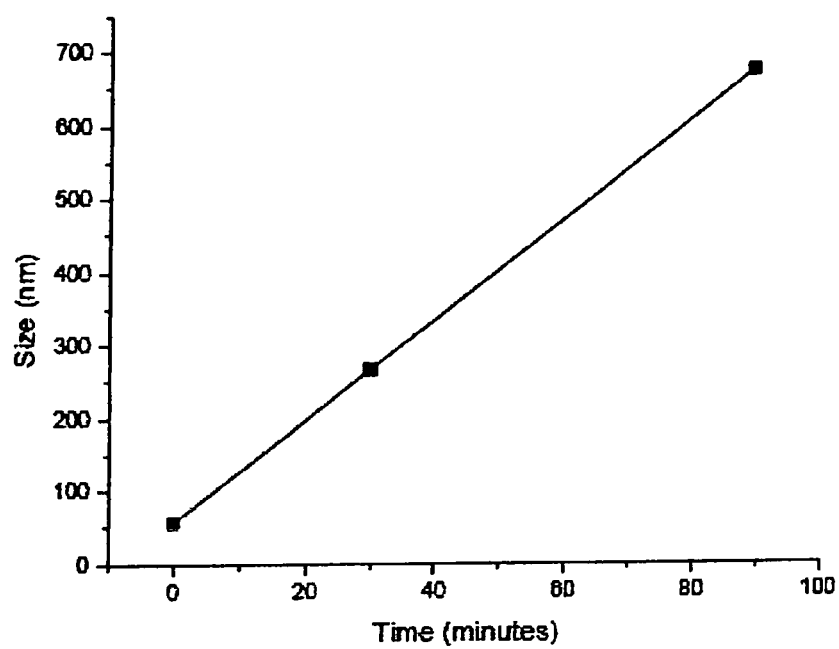
FIG. 8 is a graph showing the increase in particle size with time upon concanavalin addition.

Briefly, an aqueous solution of cerium nitrate and dextran is added to an ammonia solution under continuous stirring. Upon formation of the cerium oxide nanocrystals, molecules of dextran coat the nanoparticle surface, preventing further growth and resulting in dextran coated nanoceria. FIG. 8 shows time dependent size increase that is observed on concanavalin A induced clustering of dextran nanoceria in phosphate buffered saline (PBS).

Figure 15:
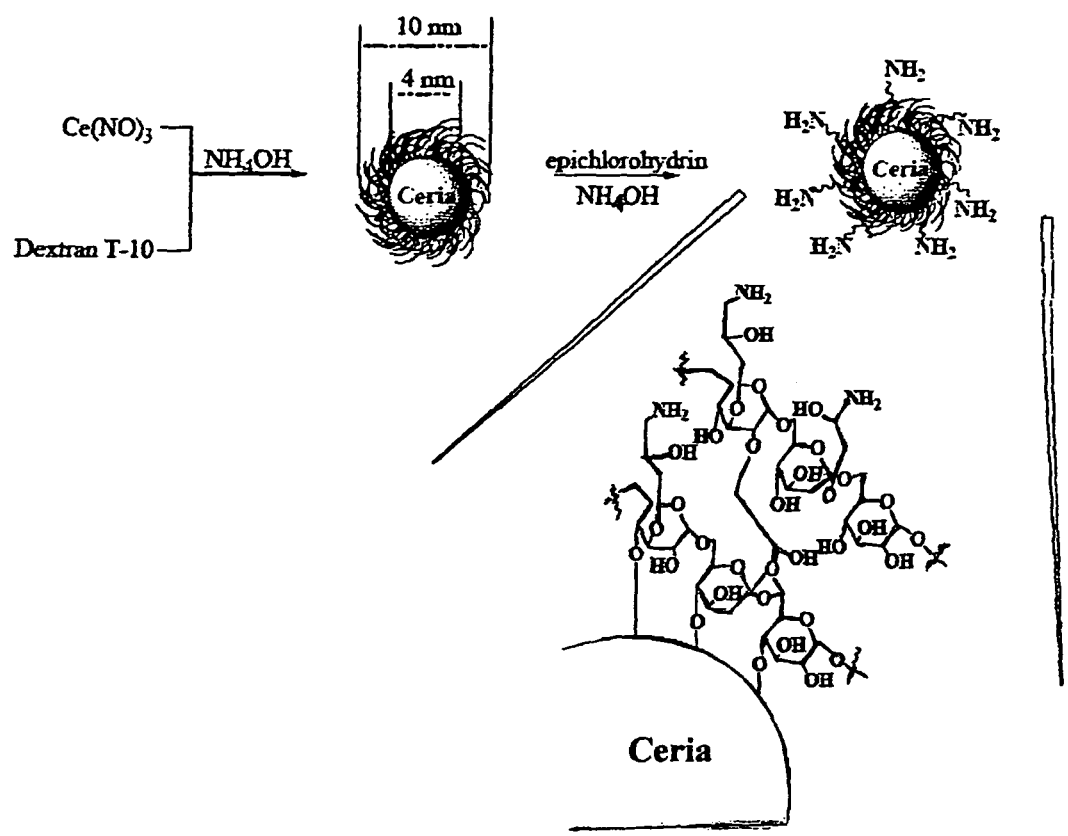
FIG. 15 is a Fourier Transform Infrared (FT-IR) spectra of pure dextran and dextran-coated cerium oxide nanoparticles.

Further stabilization and functionalization of the nanoparticle is achieved by crosslinking the dextran coating with epichlorohydrin, followed by treatment with ammonia to yield aminated dextran-coated nanoceria (ANC) as illustrated in FIG. 15.

Methods of preparing the biodegradable polymer coated cerium oxide compositions for use as an antioxidant and protection from damaging ultra violet (UV) radiation are provided in detail below.

The first embodiment of the present invention provides an in situ method and procedure for synthesizing a biodegradable polymer coated ceria nanoparticle for antioxidant and autocatalytic biomedical applications.

The second embodiment of the present invention provides a method and procedure for synthesizing aminated crosslinked dextran coated ceria nanoparticles for antioxidant and autocatalytic biomedical applications.

The third embodiment of the present invention provides a method and procedure for synthesizing non-crosslinked, carboxylated polymer coated ceria nanoparticles to provide an amine functionalized nanoparticle for antioxidant and autocatalytic biomedical applications.

The examples below provide further detail on the synthesis and physical characterization of the biodegradable polymer coated ceria nanoparticles of the present invention. Dextran is used as an exemplary polymeric coating, not a limitation of the present invention; other biodegradable polymers may be judicially selected by a person of skill in the art.

Example 1

Synthesis of Dextran Coated Ceria Nanoparticles

Under ambient conditions, a 1 M cerium nitrate solution (2.17 g in 5 ml of water) was mixed with a 1M Dextran T-10 (5 g in 10 ml of water) to form mixture (I). Under continuous stirring, the mixture (I) is then added dropwise to 30 ml of 29% ammonium hydroxide solution (Fischer, USA) forming mixture (II). Mixture (II) is then stirred continuously for 24 hours. After 24 hours of stirring, the solution turns from a light yellow to a deep brown color. The preparation is centrifuged at a rate of 4000 rpm for two 30-minute cycles to settle down any debris and large particles. The preparation is then purified from free dextran by ultrafiltration using a 30 K Amicon filter.

Example 2

Crosslinking and Amination of Dextran Coated Ceria with Epichlorohydrin

Dextran coated ceria nanoparticles are crosslinked with epichlorohydrin using the following procedure under ambient conditions:

To 3 ml (3 volume) of dextran coated nanoceria particle preparation in Example 1, 5 mL (5 volumes) of 5M NaOH are added while stirring. Then, 2 mL (2 volumes) of epichlorohydrin are added to the stirring solution. The ceria nanoparticle suspension is stirred vigorously for 8 hours at room temperature. Then, 8.5 mL (8.5 volumes) of 30% ammonia is added and stirred overnight at room temperature. The next day, the excess epichlorohydrin and ammonia are removed by ultrafiltration and the nanoparticle buffer is exchanged to 0.025 M Na-Citrate buffer pH 8. At this point, the aminated dextran nanoceria preparation can be concentrated without precipitation of the nanoparticles.

Epichlorohydrin is used as the crosslinking agent in Example 2, however, it is understood by those skilled in the art that other crosslinking agents may be used, such as glutaraldehyde, bromide derivatives of cyanogens and the like.

The dextran-coated nanoceria (DNC) and aminated dextran-coated nanoceria (ANC) preparations are both stable in water and phosphate buffered saline (PBS) at concentrations of 40 mM or higher with no precipitation for months. DNC and ANC demonstrate good water stability even after several heating cycles (70 to 80° C.) and no sedimentation of nanoparticles in PBS or citrate buffer is observed upon centrifugation at 8,000 rpm for 30 minutes. These characteristics make the water-based in situ method advantageous over organic solvent based preparations, which are prone to aggregation when suspended in aqueous media. The ANC preparation has, on average, 3.4 mM of amine per gram of cerium that could be used to conjugate targeting ligand and dyes to allow optical tracking of the nanoparticles.

It is a primary concern that the physical properties of the biodegradable polymer coated ceria nanoparticles remain unaffected by the coating which improves handling and application for biomedical purposes.

Figure 1:
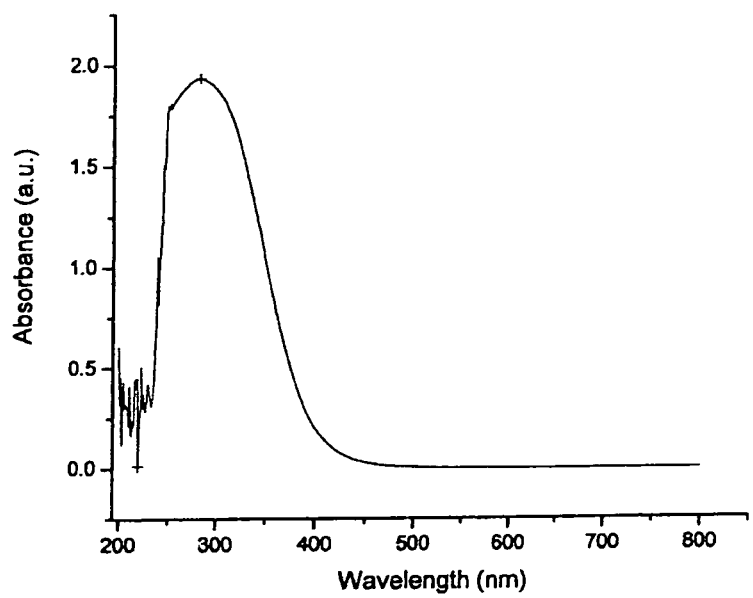
FIG. 1 shows the UV-visible absorption spectrum of the dextran coated nanoceria prepared in the present invention.

In FIG. 1, the UV profile for the dextran coated nanoceria is shown. Dextran coated ceria particles show strong absorption below 400 nm with peak absorption maximum at 300 nm. The UV profile of the dextran coated nanoceria prepared in the present invention is similar to that obtained in previous work showing that naked or uncoated ceria nanoparticles have well defined peak absorption around 305 nm. Thus, the UV profile of the coated and uncoated nanoceria is substantially the same.

Figure 2:
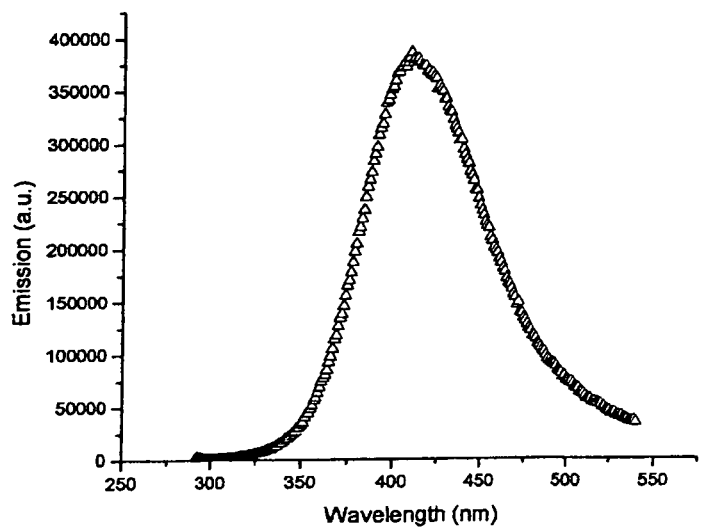
FIG. 2 is the fluorescence spectra of dextran coated cerium oxide nanoparticles ($\lambda_{ex}$=283 nm) showing a characteristic fluorescence peak at approximately 410 nanometer (nm) wavelength.

In FIG. 2 the fluorescence spectra of dextran coated nanoceria particles of the present invention has a characteristic fluorescence peak around 410 nm and is similar to the fluorescence spectra of the uncoated nanoceria particles reported by S. Sathyamurthy et al. in "Reverse Micellar Synthesis of Cerium Oxide Nanoparticles" *Nanotechnology* 16 (2005) 1960-1964.

To analyze the stability of nanoparticle preparation against agglomeration within biological systems, zeta-potential measurement is performed. In pure water, the zeta-potential measurements of oxide dispersions cover a wide range from −25 to 55 mV.

Figure 3:
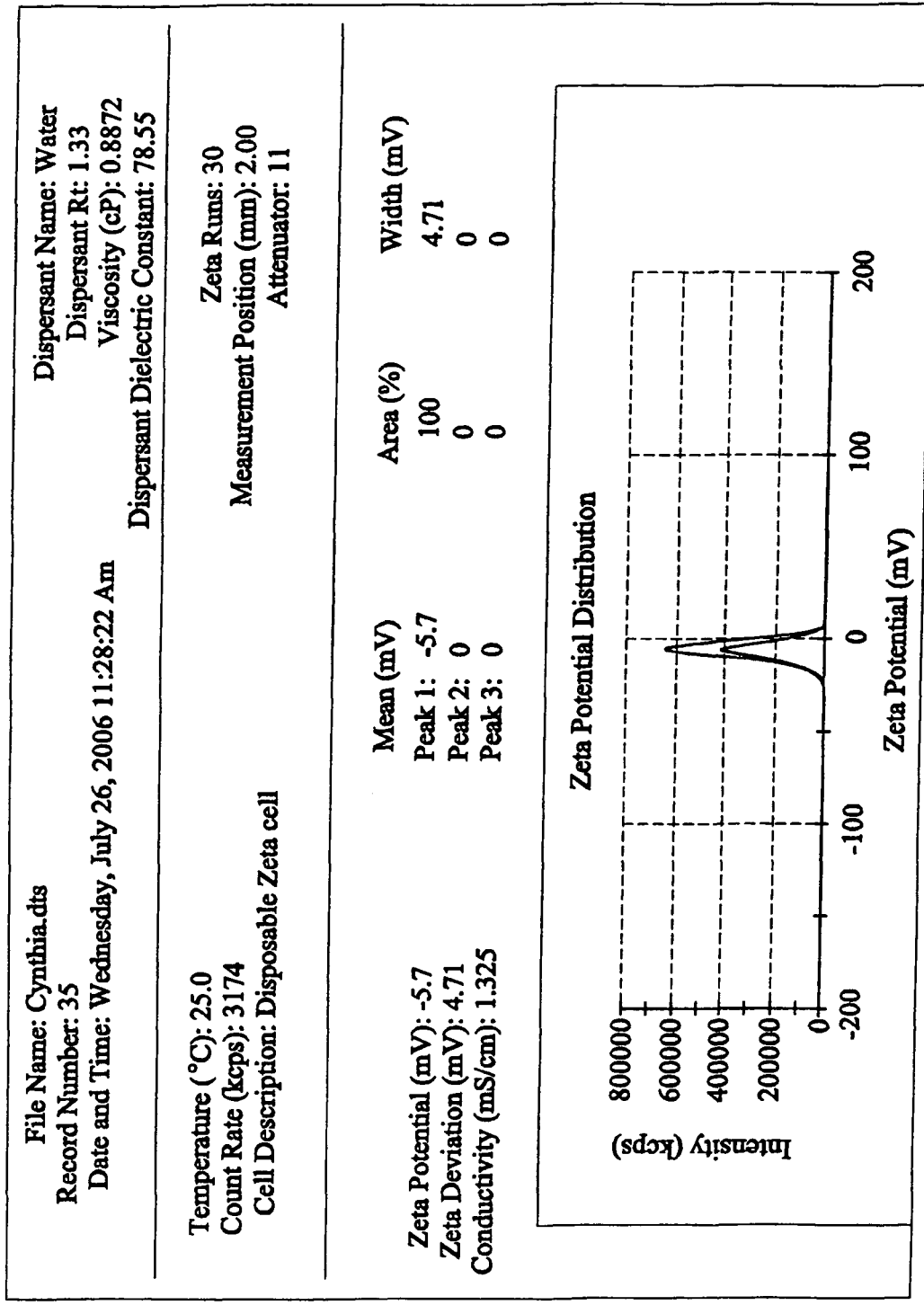
FIG. 3 shows the measurement of zeta-potential in the analysis of the stability of nanoparticle preparation against agglomeration within biological systems.

Due to the presence of dextran polymer on the surface of the nanoparticle, its charge distribution would be affected and the zeta potential would be shifted toward more positive and less negative values. The dextran coated nanoceria preparation of the present invention has a zeta potential of −5.7 mV as shown in FIG. 3.

Figure 4:
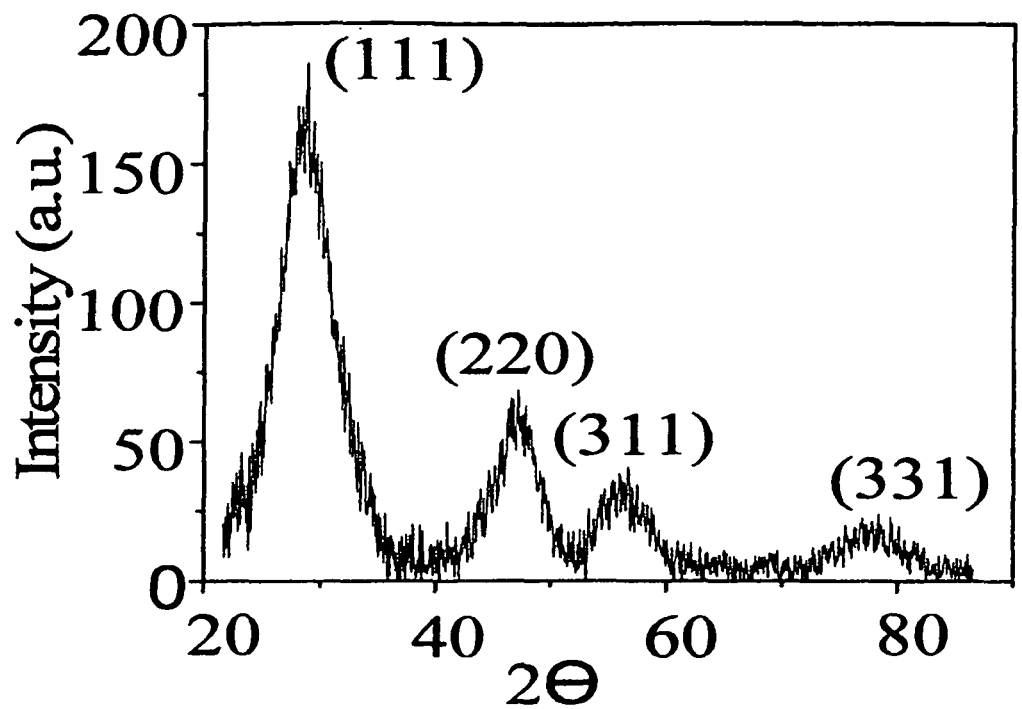
FIG. 4 shows the X-ray diffraction pattern of nanocrystalline cerium oxide coated with dextran in the present invention.

The X-ray diffraction (XRD) pattern for the dextran coated nanoceria is shown in FIG. 4. The diffraction peaks found in the coated nanoceria are in a good agreement with those found in bulk ceria and preparation of uncoated nanoceria, as determined by the earlier investigator (W. Chengyun et al, 2002, S. Sathyamurthy et al, 2005). The broadening of the peak suggests that the particles are of small dimension. The particle size, which can be calculated using the Scherrer equation, is around 3 nm, which is in agreement with the data obtained by TEM. Also XRD (X-ray diffraction) confirms that coated nanoceria particles have (111), (220), (311) and (331) planes which are in good agreement with the lattice planes identified by selected-area electron diffraction (SAED).

Figure 5:
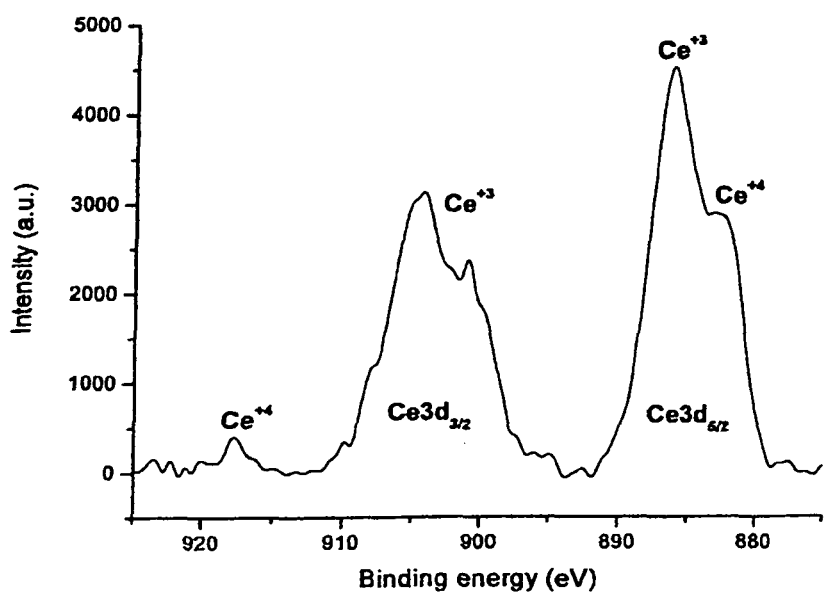
FIG. 5 shows the X-ray photon spectroscopy spectrum of the synthesized cerium oxide nanoparticles coated with dextran showing the presence of a mixed valence (Ce3+ and Ce4+) state.

X-ray photon spectroscopy (XPS) data in FIG. 5 show the presence of a mixed valence state, indicating that the dextran coating on the nanoparticle does not affect the mixed valence state, a key physical property of nanoceria. The data also show that the amount of $Ce^{+3}$ ion in the nanoparticle is more than the amount of $Ce^{+4}$ ion, in agreement with the small particle size (of less than 5 nm) as reported by D. Schubert et al., *Biochemical and Biophysical Research Communications* 2006, 342, 86. In addition, dynamic light scattering (DLS) studies revealed a monodisperse size distribution for DNC with an average diameter of approximately 10 nanometers (nm).

FIG. 6A is a photographic image of a sample of dextran nanoceria in aqueous solution wherein the vial on the left corresponds to a solution of dextran nanoceria obtained following the procedure we are disclosing in this invention disclosure, after ultrafiltration with an Amicon 30 K filter as described in Example 1. When a sample of this solution is concentrated using a 30K Centricon concentrator, a more concentrated dextran coated nanoceria is obtained, as shown in FIG. 6B, the vial on the right, with a darker solution. No precipitation of agglomeration is observed in any of the two solutions, showing the great stability of this nanoceria preparation in aqueous solution.

Figure 7A:
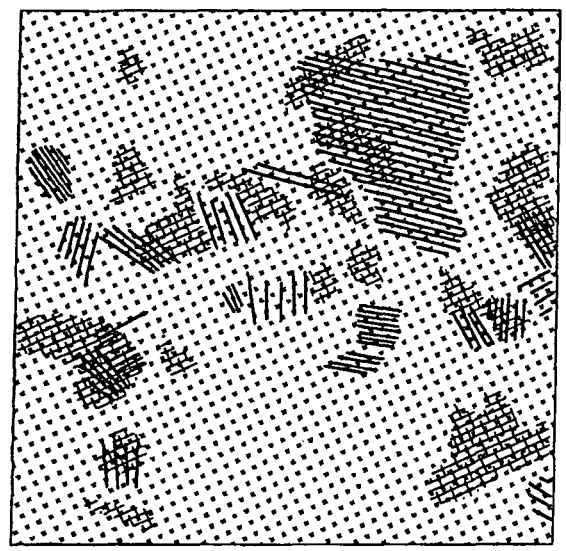
FIG. 7A is a transmission electron microscopy (TEM) image of the dextran coated ceria nanoparticles showing the size and dispersity of the ceria crystals.
Figure 7B:
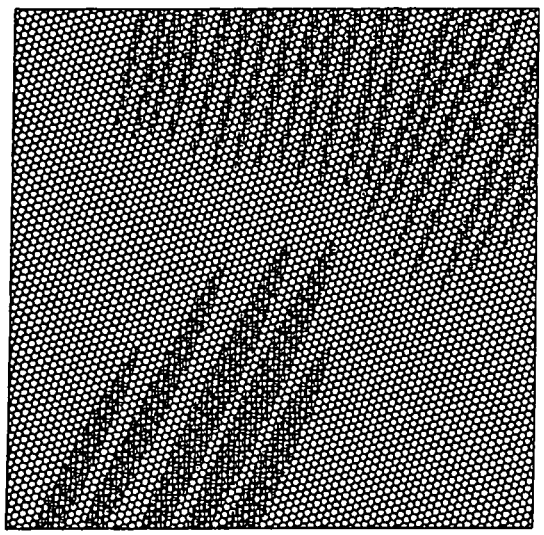
FIG. 7B is a high resolution transmission electron microscopy (HRTEM) image of the dextran coated ceria nanoparticles showing that the coating does not affect the crystallinity.
Figure 7C:
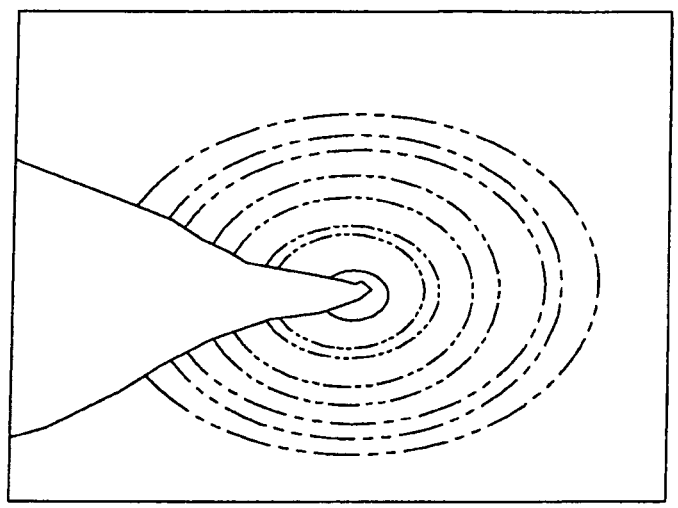
FIG. 7C is a selected area electron diffraction (SAED) image of a single ceria crystal showing that the dextran coated ceria crystal is a face-centered cubic (FCC) phase crystal.

Further characterization of the dextran coated nanoceria preparation is provided in FIGS. 7A, 7B and 7C showing the high crystallinity of the nanoceria particles of the present invention. FIG. 7A is a transmission electron microscopy (TEM) image of the dextran coated ceria nanoparticles showing the size and dispersity of the ceria crystals. FIG. 7B is a high resolution transmission electron microscopy (TEM) image of the dextran coated ceria nanoparticles, showing that the coating does not affect the crystallinity. FIG. 7C is a selected area electron diffraction (SAED) image of a single ceria crystal showing that the dextran coated ceria crystal is a FCC phase crystal.

Concanavalin A studies were used to verify the dextran coating of the ceria nanoparticles of the present invention. Concanavalin A is a protein with four binding sites, known to bind carbohydrates. This protein has been used to induce the clustering of dextran-coated gold nanoparticles and most recently it was used in the clustering of iron oxide nanoparticles. It is used to study how the clustering phenomenon changes the optical (gold nanoparticles), or magnetic (iron oxide) properties of the nanoparticles. It is used to verify whether the dextran is associated to (coating) the nanoparticle. In these studies, dextran coated nanoceria is incubated with concanavalin A and a time-dependent increase in the particle size is observed as measured by dynamic light scattering (DLS). This increase in "size" by light scattering is not due to an increase in the size of the nanoparticles, but rather is due to the clustering of the nanoparticles in solution. FIG. 8 shows that after 90 minutes incubation with concanavalin, nanoparticle clusters of 650 nm in size are observed thus, showing the increase in particle size with time upon concanavalin addition.

The addition of glucose to the nanoceria preparation before concanavalin incubation abrogated the assembly of the nanoparticles, suggesting that the observed changes in particle size distribution were due to the concanavalin-dextran interaction on the nanoparticle surface.

Figure 9:
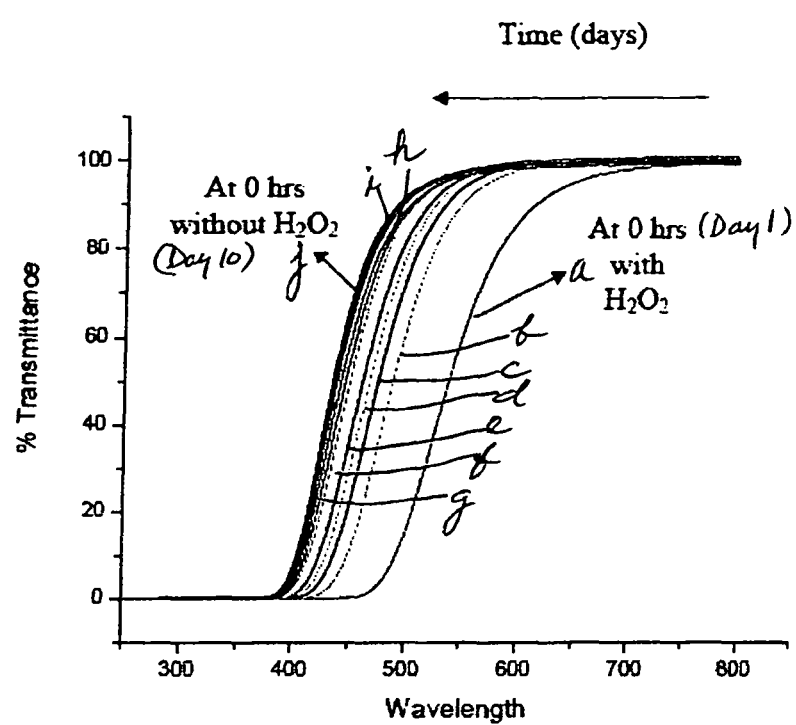
FIG. 9 is a graph showing reversible and successive shift in transmittance of dextran coated nanoceria particles after adding hydrogen peroxide (Days 1-10).

Autocatalytic behavior of dextran-coated nanoceria was studied with addition of hydrogen peroxide. One of the most interesting properties of nanoceria is its autocatalytic behavior. The ability of these nanoparticles to reversibly switch from $Ce^{+3}$ to $Ce^{+4}$, is a key factor for their biological applications as an antioxidant, among others. Therefore, it is determined whether the dextran coating on the nanoceria preparation compromised its autocatalytic behavior. In these experiments, the nanoparticles are oxidized using hydrogen peroxide. It is observed that after adding hydrogen peroxide, as an oxidizer, to the nanoceria there is a red shift and also color changes to dark orange/brown ($Ce^{+4}$). As the hydrogen peroxide decomposes from the nanoparticle suspension, the observed brown color starts to disappear and the solution color returns to yellow ($Ce^{+3}$) within ten days as shown in FIG. 9. In FIG. 9, note the reversible and successive shift in transmittance of dextran coated nanoceria particles after adding hydrogen peroxide on day one a, % transmittance plotted against the wavelength, is between approximately 475 nm to approximately 700 nm, at day 2 b, % transmittance is between approximately 410 nm to approximately 600 nm, day 3 c, % transmittance is between 400 nm and approximately 550 nm; days 4-10 d-j, after the addition of hydrogen peroxide and the decomposition of hydrogen peroxide nears completion, the plot of the % transmittance against wave length is within a narrower range between approximately 400 nm and approximately 450 nm wavelength, confirming the disappearance of the brown color.

Autocatalytic activity is represented in Equation (1) below:

$$2Ce^{+3}(aq) + H_2O_2 + 2H+(aq) \rightarrow 2Ce^{+4}(aq) + 2H_2O \qquad (1)$$

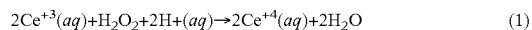

FIGS. 10A-10F are real-time images of dextran coated nanoceria solutions with and without hydrogen peroxide. FIG. 10A shows a dextran-coated nanoceria solution without hydrogen peroxide on the left 5 and with hydrogen peroxide on the right 10 at day one. FIG. 10B shows a dextran-coated nanoceria solution without hydrogen peroxide on the left 15 and with hydrogen peroxide on the right 20 at day three. FIG. 10C shows dextran nanoceria solutions without hydrogen peroxide on the left 25 and with hydrogen peroxide on the right 30 at day seven. FIG. 10D shows dextran nanoceria solutions without hydrogen peroxide on the left 35 and with hydrogen peroxide on the right 40 at day ten. FIG. 10E shows dextran nanoceria solutions without hydrogen peroxide on the left 45 and with hydrogen peroxide on the right 50 at day ten after adding fresh hydrogen peroxide on the tenth day. FIG. 10F shows dextran nanoceria solutions without hydrogen peroxide on the left 55 and with hydrogen peroxide on the right 60 at day twenty. The real-time images confirm the autocatalytic activity shown in FIG. 9; there are color changes as the hydrogen peroxide decomposes from contact with the nanoparticle suspension.

FIGS. 9, 10A to 10F demonstrate the reversibility of the antioxidant activity of polymer-coated nanoceria solutions at normal physiological conditions. Subsequent addition of hydrogen peroxide in FIG. 10E, after 10 days, brought the color of the solution back to orange/brown which again started to disappear within the next 10 days (FIG. 10F). This reversible and cyclical autocatalytic behavior at physiological conditions is essential for free radical scavenging and antioxidant properties of nanoceria and its potential medical applications.

With regard to biological activity, preliminary biological data shows that, as expected, the dextran-coated nanoceria preparation act as potent antioxidant agents. In these experiments, normal human cell cultures are exposed to hydrogen peroxide. This treatment causes a high level of cellular stress, similar to that experienced by cells under oxidative damage. The data show that in the absence of dextran nanoceria (DNC), from approximately 50% to approximately 95% of the cells died upon addition of hydrogen peroxide, whereas most of them survive this harsh treatment when in the presence of dextran coated nanoceria (DNC).

FIGS. 11A and 11B are graphs of percent viability of normal cell cultures, cardiomyocytes and dermal fibroblast, respectively. In FIGS. 11A and 11B, the control is untreated and thus 100% viable; the cells treated with dextran coated nanoceria (DNC) are 100% viable and the cells treated with a combination of dextran coated nanoparticles (DNC) and hydrogen peroxide are 100% viable. However, FIG. 11A shows that normal cell cultures of cardiomyocytes are approximately 5% viable when treated with or exposed to only hydrogen peroxide and FIG. 11B shows that normal cell cultures of dermal fibroblasts are approximately 50% viable when treated with hydrogen peroxide without dextran coated ceria nanoparticles (DNC). Thus, FIGS. 11A and 11B are graphical illustrations of the effectiveness of dextran coated ceria nanoparticles as potent antioxidant agents that promote 100% cell viability in the presence of deadly oxidizing agents.

The crosslinking and amination of dextran coated ceria with epichlorohydrin as discussed in Example 2 above, was studied to determine whether the anti-oxidant properties of the nanoceria particles could be extended to injectable or targetable biomedical applications.

The dextran coated nanoceria prepared according to Example 1 shows great stability in water and various aqueous buffers, such as 0.1 M phosphate buffer, pH 7.4, without compromising its autocatalytic and antioxidant properties. However, the surface of this nanoparticle cannot be easily modified with targeting ligands such as peptides, oligonucleotides and proteins. To advance these studies, the polymeric dextran coating has been crosslinked on the surface of the ceria nanoparticle using epichlorohydrin and further derivatized its surface with ammonia to yield an aminated dextran coated nanoceria. As discussed earlier, it is known in the art to use other crosslinking agents and the present invention incorporates by reference, other known crosslinking agents, such as, but not limited to, glutaraldehyde, bromide derivatives of cyanogens, and the like.

Preliminary characterization of this preparation shows that indeed the dextran surface contains reactive amino groups that can be used to conjugate targeting ligands and various dyes, including near infrared dyes that would allow in vivo optical tracking of the nanoparticle. Furthermore, this amine group, which has a positive charge at physiological pH, can be reacted with a succinic anhydrate, resulting in a carboxylated or negatively charged nanoceria preparation, greatly expanding the conjugation capabilities of the aminated preparation.

Figure 12:
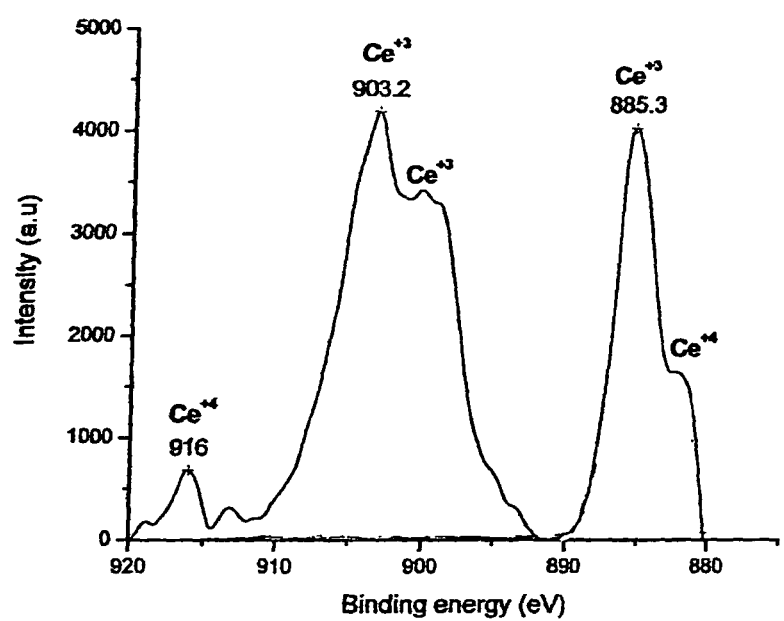
FIG. 12 is an X-ray photon spectroscopy (XPS) spectra of the aminated nanoceria showing the presence of a mixed valence, $Ce^{+3}$ and $Ce^{+4}$ similar to the spectrum of dextran coated nanoceria that is not aminated.

FIG. 12 is an X-ray photon spectroscopy (XPS) spectrum of the aminated crosslinked nanoceria showing the presence of a mixed valence, $Ce^{+3}$ and $Ce^{+4}$ similar to the spectrum of dextran coated nanoceria that is not aminated.

Physical properties of the aminated dextran coated nanoceria were analyzed by X-ray photon spectroscopy to determine whether the crosslinking procedure would affect the presence of both $Ce^{+3}$ and $C^{+4}$ and therefore its biological and autocatalytic activity. As shown in FIG. 12, the presence of both $Ce^{+3}$ and $Ce^{+4}$ species in the aminated dextran coated nanoceria are similar to those obtained with non-crosslinked nanoceria. This indicates that crosslinking of the dextran does not affect the dual valency ($Ce^{+3}/Ce^{+4}$) in the nanoceria preparation of the present invention and most likely will not affect its autocatalytic/antioxidant properties. Biological uses of the crosslinked, biodegradable polymer-coated nanoceria include administration to human and other mammals needing antioxidant treatments to prolong cell life.

Example 3

Carboxylated Polymer Coating of Nanoceria Particles

In another embodiment, following the procedure outlined in Example 1, wherein under ambient conditions, a 1 molar solution of a polyacrylic acid is used in place of the 1 molar solution of dextran, nanoceria particles are coated with a biodegradable polymer containing a plurality of carboxylic groups (carboxylated polymer), wherein a portion of the carboxyl groups are associated with the cerium oxide surface and a portion of carboxyl groups are exposed on the nanoparticle surface and available for conjugation. The carboxylated nanoparticle can be reacted with a diamine, such as ethylene diamine, and correspondingly converted to an amine functionalized nanoparticle.

Synthesis Method.

The preparation of polyacrylic acid coated nanoceria (PAA-nanoceria) involves the use of cerium (III) nitrate and polyacrylic acid (PAA). 1 M cerium (III) nitrate (Aldrich, 99%) solution (2.17 grams in 5.0 milliliters (ml) of water) was mixed with 0.5 mM solution of PAA (Sigma) to form mixture (I). With continuous stirring, the cerium nitrate and PAA mixture (I), is added drop wise to 30.0 ml of 29% ammonium hydroxide (Sigma Aldrich, 30%) solution to form mixture II. Subsequently, mixture (II) is stirred continuously for 24 hours; at this point, the solution has changed from a light yellow to a deep brown color. Next, the stirred mixture (II) is centrifuged at 4000 rpm for two 30 minute cycles to settle down any debris and large particles. The centrifuged solution is then purified from free PAA by ultrafiltration using 30K molecular weight cut-off Amicon filter (Millipore, Inc.) The resulting negative charge on the PAA-nanoceria is assessed by zeta potential analysis.

Below is a schematic diagram (2) of the synthesis of polyacrylic acid coated nanoceria (PAA-nanoceria).

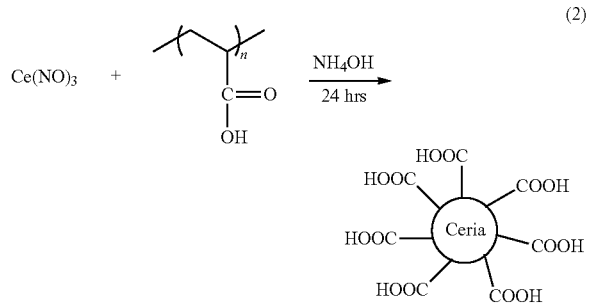

(2)

Note that the nanoparticles are functionalized with carboxylic groups on the surface, which allows conjugation of peptides, DNA oligonucleotides, proteins, antibodies and small molecules for targeting applications, without the need for crosslinking the polymer.

Furthermore, the carboxylic groups on the polyacrylic acid nanoceria can be converted to reactive amine groups by the reaction with a water soluble diamine, such as ethylene diamine, in the presence of a water soluble carbodiimide as disclosed in Gaw et al., U.S. Patent Publication 2002/0124194 for coating of iron oxide nanoparticles as MRI contrast agents.

Figure 13:
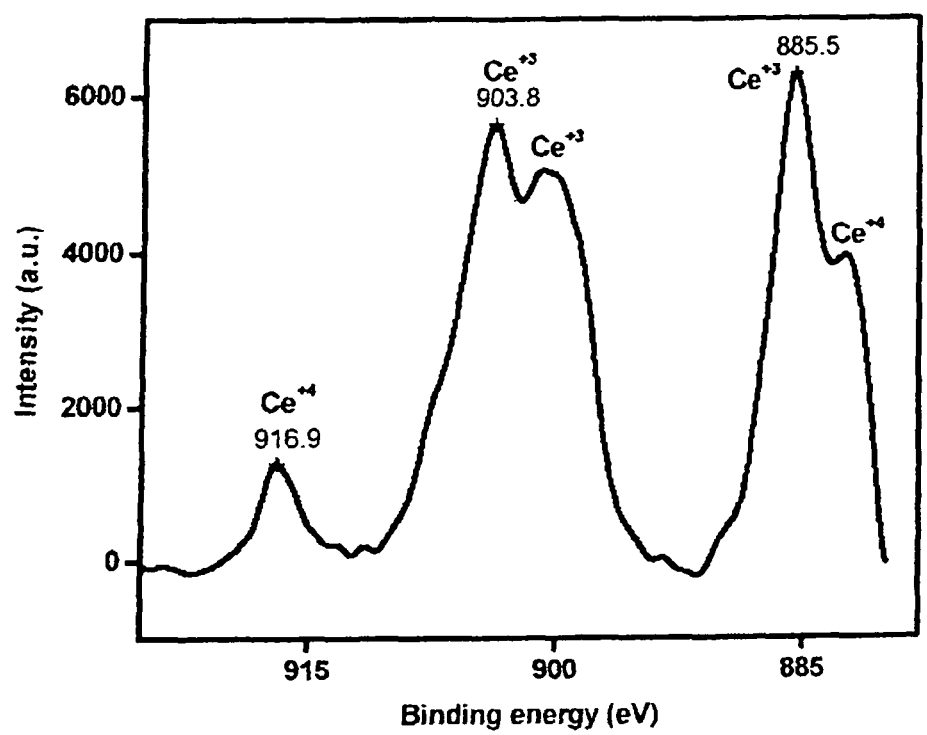
FIG. 13 is an X-ray photon spectroscopy (XPS) spectrum of the polyacrylic acid coated nanoceria (PAA-nanoceria) showing the presence of a mixed valence, $Ce^{+3}$ and $Ce^{+4}$ similar to the spectrum of dextran coated nanoceria and aminated dextran coated nanoceria shown in FIG. 12.

PAA-nanoceria possesses similar autocatalytic activity as regular, non-coated nanoceria, dextran coated nanoceria, and aminated dextran coated nanoceria. In addition, PAA-nanoceria contains both $Ce^{4+}$ and $Ce^{3+}$ (mixed valance) on the nanoparticle which is important for its autocatalytic and antioxidant activity as shown in FIG. 13. The X-ray photon spectroscopy (XPS) image of polyacrylic acid coated nanoceria (PAA-nanoceria) in FIG. 13 is substantially similar to the X-ray photon spectroscopy (XPS) image of dextran coated nanoceria and aminated dextran coated nanoceria shown in FIG. 12. This indicates that the PAA-nanoceria will behave like the other polymer coated nanoceria preparations disclosed herein.

Prior to the present invention, a facile, cost effective, non-toxic synthesis of biodegradable polymer coated nanoceria particles was not available. The synthesis does not require surfactants or vigorous experimental conditions and the end-product is suitable for unlimited biomedical applications.

Prior to the present invention, it was not known that a biodegradable polymeric coating of ceria nanoparticles would not affect the autocatalytic and antioxidant properties of the ceria nanoparticles.

A biodegradable polymer coated nanoceria exhibits good solubility and stability in water and phosphate buffer saline. The preparation has good stability over many days in the buffer solution which is advantageous over the preparations which aggregate when redispersed in aqueous media. This characteristic makes them suitable for biomedical applications and clinical use. Further, there is no problem with agglomeration in aqueous solution over a long period of time, as with preparations using a sol-gel technique as reported by H. S. Potdar et al. in *Materials Chemistry and Physics*, 2002 74, 306.

Further advantages of the biodegradable polymer coated cerium oxide nanoparticle include a suspension that can be concentrated using ultrafiltration devices without agglomeration of the nanoparticles.

With regard to the second embodiment, the dextran coating on the nanoparticle can be crosslinked with epichlorohydin and ammonia, resulting in an aminated dextran coated ceria nanoparticles. The major benefit of the crosslinked dextran coating is the ability to form conjugates with various ligands, such as peptides, antibodies, DNA-oligonucleotides, proteins and small molecules, to create a targetable ceria nanoparticle. This would allow targeting or "homing" of the nanoparticle to the corresponding site of inflammation or disease.

All embodiments of the present invention are useful in forming colloidal compositions which include nanoparticle suspensions of cerium oxide coated with a biodegradable polymer. The resulting colloidal composition is highly stable in water and water-based buffers, such as phosphate saline buffer and the like. The colloidal compositions are also suitable for concentration and sterilization by filtration.

Similar procedures have been used in the preparation of carboxylated coated iron oxide nanoparticles, allowing for the creation of targeted molecular imaging agent for MRI as reported in Gaw et al. U.S. Patent Publication 2003/0124,194; the teaching with regard to use of carboxylated polymers is incorporated herein by reference.

Some dextran coated iron oxide nanoparticles have been approved by the FDA for various applications including MRI imaging of lymph nodes as reported by M. G. Harisinghani, et al. in *New England it of Medicine* 2003, 348, 2491.

The newly developed synthesis of biodegradable polymer coated ceria nanoparticles presented herein would be ideal for clinical applications and a candidate for FDA approval. It was an unexpected finding that the physical properties of the biodegradable polymer coated ceria nanoparticles remain unaffected by the polymeric coating which substantially improves handling and application for antioxidant and autocatalytic biomedical applications.

Figure 16:
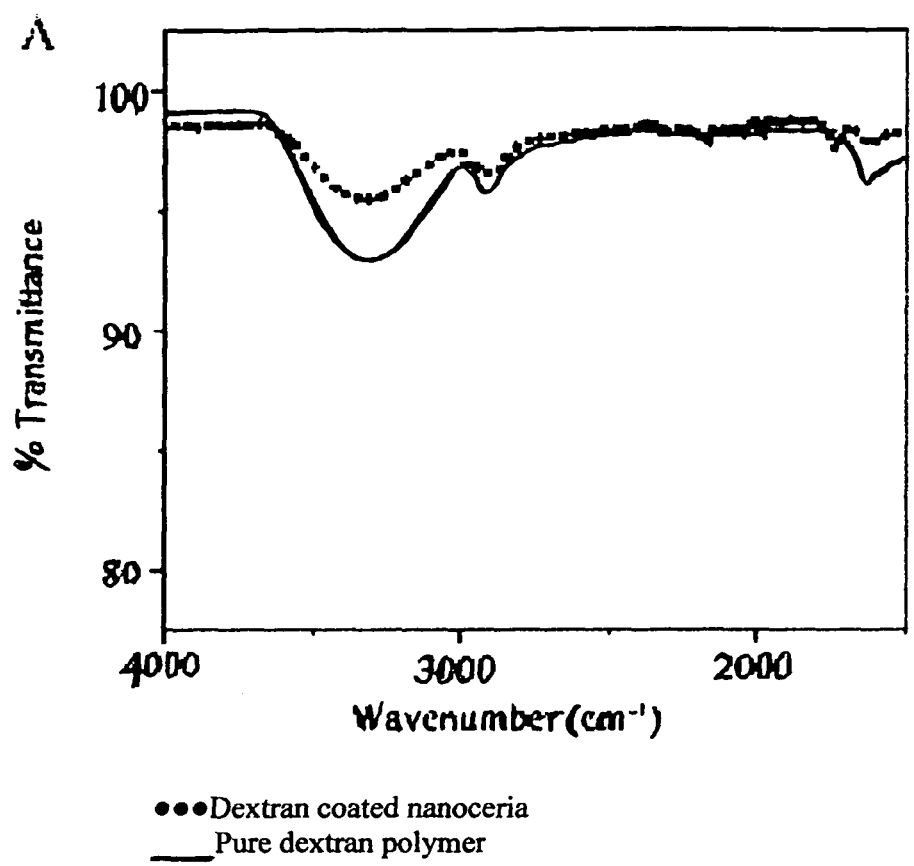
FIG. 16 is an FT-IR spectra of a representative dextran coated nanoceria preparation compared to that of pure dextran, indicating the presence of characteristic dextran IR bands in dextran coated nanoceria.

Thus, polymer-coated and functionalized nanoceria particles show great stability with no precipitation for more than six months stored at room temperature. FT-IR spectra shown in FIG. 16 confirms the presence of dextran coating on the coated ceria nanoparticles confirming that dextran is a vital part of the nanoparticles, since characteristic IR peaks of dextran are also present in the dextran-coated nanoceria (DNC) spectrum. The FT-IR analysis reveals the presence of dextran in the synthesized nanoceria and substantiates the complete surface passivation of the ceria nanocrystal by dextran.

The great stability with no precipitation and the presence of dextran as an integral part of the ceria nanoparticles supports a finding of high stability of the DNC under physiological conditions and testing of dextran-coated nanoceria solution in phosphate-buffered saline (PBS) in a pH range of approximately 7.4 to approximately 11.0 where reversible antioxidant behavior is observed.

New Properties of Polymer-Coated Cerium Oxide Nanoparticles.

Figures 18, 19:
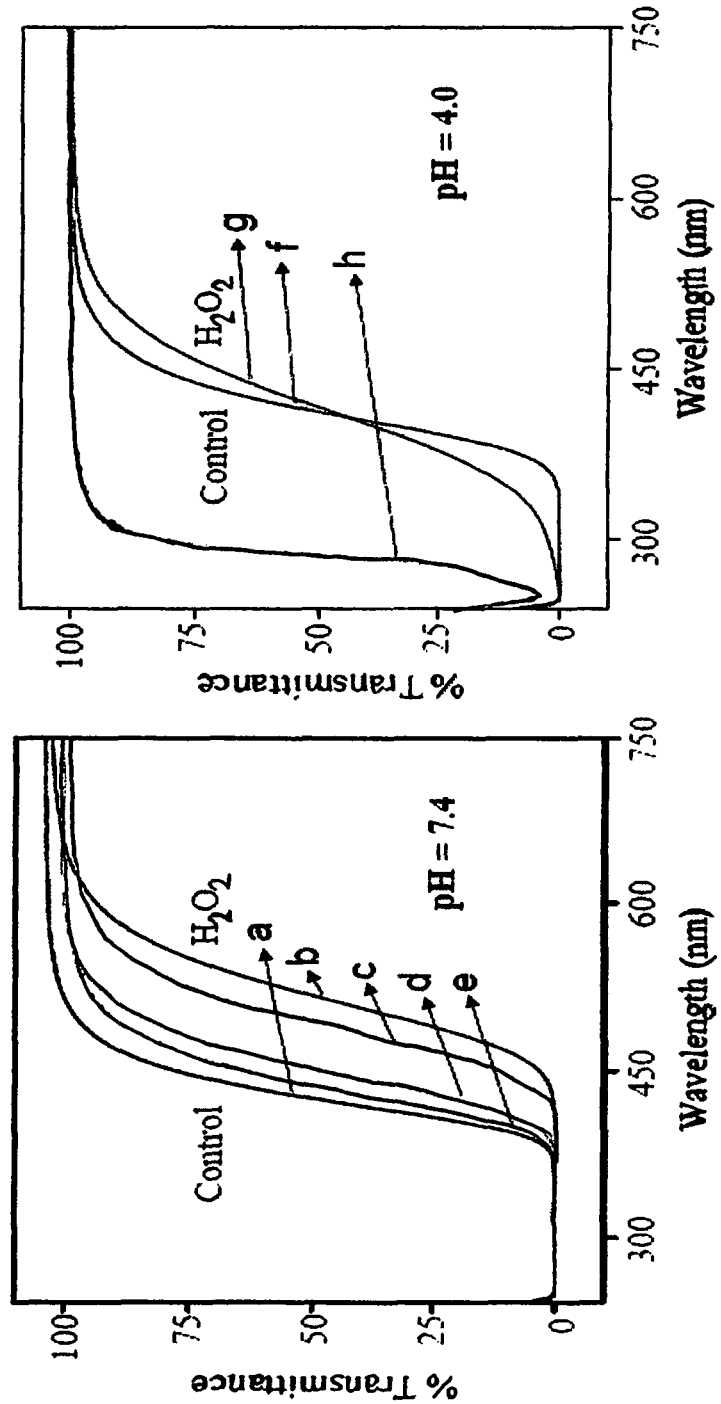
FIG. 18 is a graph of the transmittance spectra showing reversible autocatalytic behavior for dextran coated nanoceria when incubated with hydrogen peroxide at pH 7.4.
FIG. 19 is a graph of the transmittance spectra showing irreversible autocatalytic behavior for dextran coated nanoceria when incubated with hydrogen peroxide at pH 4.0.

Under acidic pH conditions, polymer-coated cerium oxide nanoparticles do not exhibit reversible antioxidant behavior. FIGS. 17B, and 19 show that at pH 4.0, the oxidation capability of dextran-coated nanoceria (DNC) is not reversible, in contrast to, FIGS. 17A and 18 where the tests were conducted at neutral pH or alkaline conditions which are comparable to physiological conditions.

In FIG. 17A, the addition of hydrogen peroxide at ten-day intervals caused the slightly yellow solution to turn to an orange/brown color, gradually returning to the slightly yellow color in a reversible cycle. FIG. 18 is the XPS spectra showing changes in % transmittance (a-e) based on the changes in the amount of $Ce^{+3}$ and $Ce^{+4}$ at pH 7.4. The control a shows transmittance before the addition of hydrogen peroxide; b shows transmittance immediately after addition of hydrogen peroxide; c is transmittance after 24 hours; d is transmittance after 3 days and e is transmittance after seven days.

FIG. 17B shows that at pH 4.0 (acidic conditions), DNC does not exhibit a significant red shift upon addition of hydrogen peroxide, even though the color of the solution has turned slightly orange. Surprisingly, after 24 hours, the solution turned completely clear and a significantly large blue shift was observed. In FIG. 19, the control f represents transmittance before the addition of hydrogen peroxide, g is transmittance immediately after addition of hydrogen peroxide and h is the transmittance curve after 24 hours and after 3 days.

After ten days, the solution remained clear and the addition of more hydrogen peroxide did not bring either the color of the solution back to orange or have any effect on the transmittance curve. Furthermore, once the pH of dextran nanoceria preparation was lowered to 4.0, the autocatalytic activity could not be reversed, even on raising the pH to 7.4, showing irreversibility at acidic pH values, such as 4.0.

Further evidence of the nonreversibility at acidic pH is shown in Table 1 below.

TABLE 1

Total amount of $Ce^{+3}$ and $Ce^{+4}$ in DNC at different pH values, as determined by XPS.[a]

| | pH 7.4 | | pH 4 | |
|---|---|---|---|---|
| | $Ce^{+3}$ [%] | $Ce^{+4}$ [%] | $Ce^{+3}$ [%] | $Ce^{+4}$ [%] |
| Initial | 53.54 | 46.46 | 54.16 | 45.84 |
| Immediately after $H_2O_2$ addition | 40.7 | 59.3 | 40.0 | 60.0 |
| 10 days after $H_2O_2$ addition | 55.9 | 44.1 | 41.4 | 58.6 |

In Table 1 above, XPS studies of DNC at pH 7.4 and pH 4.0 revealed similar amounts of $Ce^{+3}$ and $Ce^{+4}$ at both pH values in the initial samples. Upon addition of hydrogen peroxide, a similar increase in the amount of $Ce^{+4}$ was observed at both pH values. However, note that ten days after addition of hydrogen peroxide, DNC at pH 7.4 is able to regenerate returning to values for $Ce^{+3}$ and $Ce^{+4}$ similar to those in the initial sample, confirming the reversibility of the system at pH 7.4. In contrast, DNC is unable to regenerate at pH 4.0, keeping a relatively high amount of $Ce^{+4}$ after 10 days, confirming the nonreversibility of $Ce^{+3}$ and $Ce^{+4}$ values at an acidic pH.

It has been proposed that the antioxidant properties of nanoceria are due to the presence of mixed valence states ($Ce^{+3}/Ce^{+4}$) on the nanoparticle surface that allow for the scavenging of free radicals. During the scavenging process, $Ce^{+3}$ ions are converted to $Ce^{+4}$, as shown in schematic diagram (3) below.

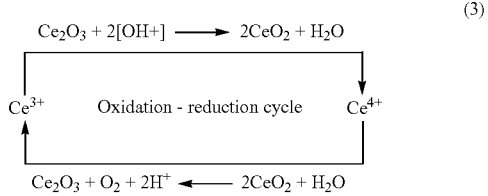

(3)

The system is regenerated via a series of surface chemical reactions between ions in solution (such as $H^+$) and the $Ce^{+4}$ ions on the nanoparticle surface, where they are converted back to $Ce^{+3}$, and therefore allows for the scavenging of more free radicals. Theoretically, the low-pH environment interferes with the cyclical regenerative or autocatalytic nature of nanoceria due to the high concentration of protons ($H+$) at low pH, and therefore inhibits the ability of nanoceria to scavenge more free radicals. This effect renders dextran nanoceria as an inefficient antioxidant at low pH.

The observed nonreversible poisoning of dextran-coated nanoceria at pH 4.0 has important implications in cancer therapy. It is well known that most tumors have acidic microenvironments due to high rates of glycolysis and lactic acid production, known as the Warburg effect. Also, since the generation of oxygen radicals (oxidative stress) occurs in both tumor and healthy tissue during radiation therapy, the dextran coated nanoceria can faciliaite pH dependent preferential protection of healthy tissue. The cancer cells are not protected against hydrogen peroxide-induced oxidative stress, due to their acidic micro-environment.

Effect of Dextran-Coated Nanoceria on Cancer Cells.

Figure 20:
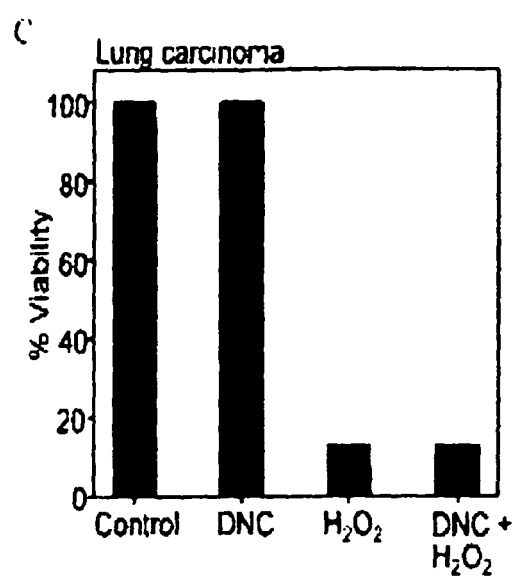
FIG. 20 shows the effect of dextran-coated nanoceria on lung carcinoma.
Figure 21:
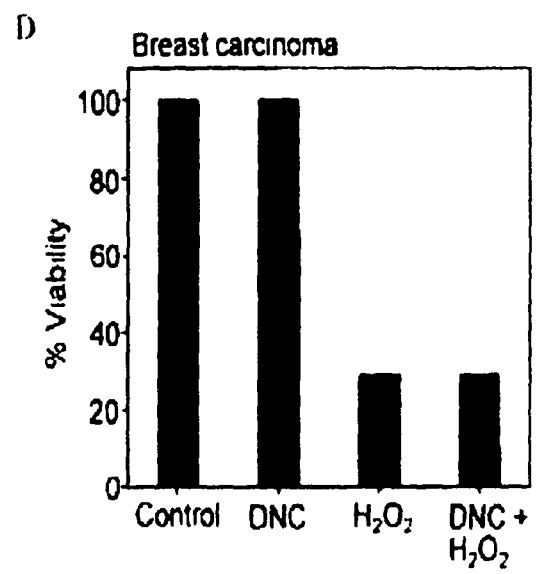
FIG. 21 shows the effect of dextran-coated nanoceria on breast carcinoma cells.

FIGS. 20 and 21 show the effect of dextran-coated nanoceria on cancer cells against hydrogen peroxide-induced toxicity. Lung cancer (A-549) cells were treated with dextran coated nanoceria before administering hydrogen peroxide (0.2M) and as shown in FIG. 20, no protection against oxidative damage is observed in lung carcinoma cells. The percentage of cell viability dropped to less than 20% and is equivalent to the cell viability when hydrogen peroxide is used without DNC.

Similar results were obtained with breast cancer (BT-474) cells. FIG. 21 shows that DNC provides no protection against oxidative damage in breast carcinoma cells; the percentage of cell viability is approximately 30% and is equivalent to cell viability when hydrogen peroxide is used to induce oxidative stress.

All data points in FIGS. 20 and 21 represent the average of three measurements with standard errors ranging between 1.0 and 2.0% which is too small to graph.

As lung and breast tumors are among the most prevalent and aggressive carcinomas, requiring extensive radiation therapy and chemotherapy, DNC can provide long-term cytoprotection to nontransformed surrounding cells, minimizing adverse side effects.

Effect of Dextran Nanoceria on Other Biologically Relevant Radicals.

Figure 22:
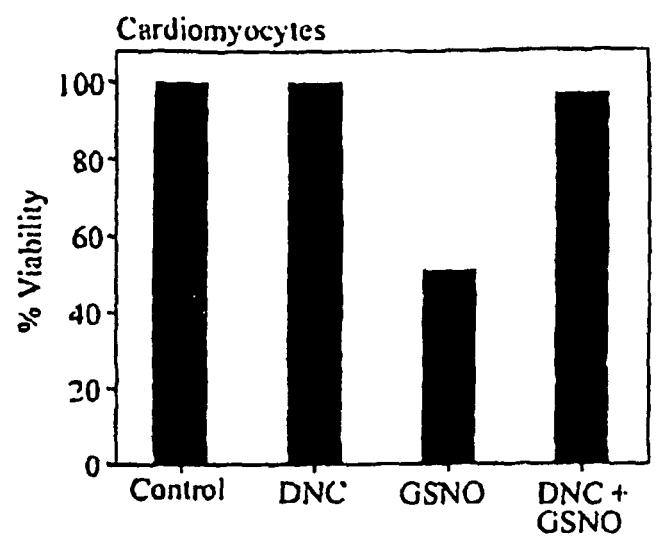
FIG. 22 is a graph showing the percent viability of normal cardiomyocyte cell cultures protected from nitroxyl radical induced toxicity when treated with dextran coated nanoparticles versus no treatment with dextran coated nanoceria.
Figure 23:
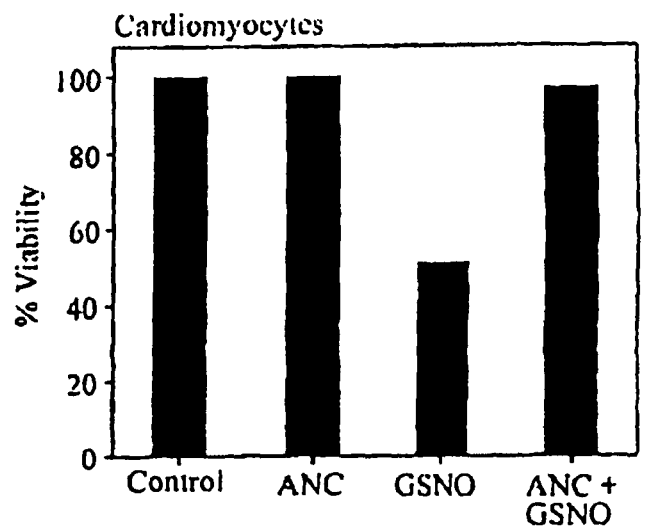
FIG. 23 is a graph showing the percent viability of normal cardiomyocyte cell cultures protected from nitroxyl radical induced toxicity when treated with aminated dextran coated nanoparticles versus no treatment with aminated dextran coated nanoceria.

The overproduction of nitric oxide resulting in nitroxyl (NO*) radicals can lead to tissue damage during inflammation associated with cardiovascular pathogenesis or heart failure. Cardiomyocytes were treated with dextran coated nanoceria in culture media containing 500 µM S-nitrogluathione (GSNO) as a nitric oxide donor. Under these conditions, NO* is released from the dissociation of GSNO in water at the rate of 5% per hour; therefore cells incubated with GSNO for 24 hours were exposed to elevated levels of NO*. Results show that both dextran nanoceria preparations effectively protected cardiomyocytes against NO*-induced oxidative stress (FIGS. 22 and 23). This supports using dextran nanoceria to protect normal tissue from nitroxyl radical-induced damage during inflammation, such as in atherosclerosis and neurodegenerative conditions.

In summary, the present invention shows that biocompatible dextran-coated nanoceria exhibit excellent, pH-dependent antioxidant properties for improved cancer therapeutics, as DNC or ANC provide cytoprotection from free radicals to normal cells but not to cancer cells, which are typically in an acidic environment. In addition, dextran-coated nanoceria can be beneficial in the treatment of inflammatory diseases such as cardiovascular diseases and arthritis.

Thus, polymer-coated nanoceria particles are provided for use as smart, pH-dependent therapeutic agents and devices that selectively protect healthy tissue from free radicals, which might be elevated during chronic inflammation or during radiation therapy and chemotherapy while permitting transformed or diseased cells in an acidic microenvironment to be eradicated. The selective protection of nontransformed, healthy cells surrounding a diseased site minimizes adverse side effects of aggressive therapeutic treatments, such as radiation therapy and chemotherapy.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A process for protecting normal, non-transformed biological cells using a pH-dependent therapeutic agent, comprising:
providing a plurality of biocompatible, polymer-coated cerium oxide nanoparticles having a pH-dependent antioxidant property, said polymer-coated cerium oxide nanoparticles being an active antioxidant in pH range from 7 to approximately 11 while having a substantially reduced antioxidant activity at an acidic pH from approximately 2 to 6, said polymer-coated cerium oxide nanoparticles not able to reversibly switch from $Ce_3^+$ to $Ce_4^+$ at said acidic pH; and
adding an effective amount of said polymer-coated cerium oxide nanoparticles to a cell environment containing normal biological cells and diseased biological cells so as to contact said normal biological cells and diseased biological cells, thereby selectively protecting said normal, non-transformed cells from hydroxyl-radical induced oxidative, nitroxyl-radical induced oxidative stress, radiation therapy, inflammation or chemotherapy, while providing no cytoprotection to said diseased cells.

2. The process of claim 1, wherein the normal biological cells have a pH value between approximately 6.5 to approximately 11.0 and the diseased biological cells have a pH value between approximately 2.0 and approximately 6.4.

3. The process of claim 1, wherein the plurality of biocompatible, polymer-coated cerium oxide nanoparticles are coated with a biodegradable polymer selected from at least one of a carbohydrate polymer, a synthetic polyol, a carboxylated polymer, and derivatives thereof.

4. The process of claim 1, wherein the polymer-coated cerium oxide nanoparticles are coated with a crosslinked-aminated biodegradable polymer selected from at least one of a carbohydrate polymer, a synthetic polyol, a carboxylated polymer and derivatives thereof.

5. The process of claim 1 wherein the normal biological cells include cardiomyocytes, dermal fibroblasts, lung tissue cells or breast tissue cells.

6. The process of claim 1, wherein the diseased biological cells include lung cancer cells, breast cancer cells, or dermal cancer cells.

7. The process of claim 3, wherein the biodegradable polymer is polyacrylic acid or polysaccharide.

8. The process of claim 7, wherein the polysaccharide is dextran.

9. The process of claim 3, wherein a colloidal suspension formed by the polymer-coated cerium oxide nanoparticles is stable in water or phosphate buffer solution.

10. The process of claim 4, wherein the biodegradable polymer is polyacrylic acid or polysaccharide.

11. The process of claim 10, wherein the polysaccharide is dextran.

12. The process of claim 4, wherein a colloidal suspension formed by the polymer-coated cerium oxide nanoparticles is stable in water or phosphate buffer solution.

* * * * *